United States Patent
Bauer et al.

(10) Patent No.: US 8,329,200 B2
(45) Date of Patent: Dec. 11, 2012

(54) COSMETIC OR DERMATOLOGICAL STICK

(75) Inventors: Anja Bauer, Hamburg (DE); Albrecht Dörschner, Hamburg (DE); Alexander Filbry, Hamburg (DE); Anja Göppel, Hamburg (DE); Ghita Lanzendörfer, Hamburg (DE); Kirsten Schneider, Hamburg (DE); Jens Schulz, Schenefeld (DE); Jörg Schreiber, Hamburg (DE); Jessica Stelling, Hamburg (DE); Mirko Tesch, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1273 days.

(21) Appl. No.: 10/812,469

(22) Filed: Mar. 29, 2004

(65) Prior Publication Data

US 2004/0258721 A1    Dec. 23, 2004

Related U.S. Application Data

(63) Continuation of application No. PCT/EP02/10904, filed on Sep. 27, 2002.

(30) Foreign Application Priority Data

| Sep. 29, 2001 | (DE) | 101 48 301 |
| Sep. 29, 2001 | (DE) | 101 48 302 |
| Sep. 29, 2001 | (DE) | 101 48 313 |
| Sep. 29, 2001 | (DE) | 101 48 314 |
| Oct. 12, 2001 | (DE) | 101 50 619 |
| Nov. 9, 2001  | (DE) | 101 55 960 |

(51) Int. Cl.
| A61K 8/02  | (2006.01) |
| A61K 8/00  | (2006.01) |
| A61K 8/18  | (2006.01) |
| A61Q 17/04 | (2006.01) |
| A61Q 1/04  | (2006.01) |
| A61Q 1/06  | (2006.01) |

(52) U.S. Cl. ............ 424/401; 424/59; 424/64
(58) Field of Classification Search ......... 424/401, 424/59, 64
See application file for complete search history.

(56) References Cited

U.S. PATENT DOCUMENTS

| 3,957,969 A | 5/1976 | Fujiyama et al. |
| 4,704,271 A | 11/1987 | Hourihan et al. |
| 4,719,103 A | 1/1988 | Krevald et al. |
| 4,725,431 A | 2/1988 | Hourihan et al. |
| 4,980,167 A | 12/1990 | Harashima et al. |
| 5,011,680 A | 4/1991 | Suzuki et al. |
| 5,085,856 A | 2/1992 | Dunphy et al. |
| 5,516,510 A | 5/1996 | Beilfuss et al. |
| 5,538,718 A | 7/1996 | Aul et al. |
| 5,672,339 A | 9/1997 | Soyama et al. |
| 5,753,212 A * | 5/1998 | Pescatore et al. ............ 424/65 |
| 5,860,756 A * | 1/1999 | Fabrisi ............ 401/78 |
| 6,040,347 A | 3/2000 | Cupferman et al. |
| 6,183,760 B1 * | 2/2001 | Travkina et al. ............ 424/401 |
| 6,274,153 B1 | 8/2001 | Bruechert et al. |
| 6,387,355 B2 | 5/2002 | Heidenfelder et al. |
| 6,409,995 B1 | 6/2002 | Habeck et al. |
| 6,613,338 B1 | 9/2003 | Schreiber et al. |
| 2002/0055562 A1 * | 5/2002 | Butuc ............ 524/80 |
| 2002/0076423 A1 * | 6/2002 | Kropke et al. ............ 424/401 |
| 2002/0146438 A1 | 10/2002 | Bleckmann et al. |

FOREIGN PATENT DOCUMENTS

| DE | 19817292 | 10/1999 |
| DE | 19933463 | 1/2000 |
| DE | 19844261 | 3/2000 |
| DE | 20009445 | 8/2000 |
| DE | 19929475 | 12/2000 |
| DE | 29919474 | 12/2000 |
| EP | 1 036 553 A2 | 9/2000 |
| EP | 1 064 908 | 1/2001 |
| GB | 1427749 | 3/1976 |
| GB | 2162439 | 2/1986 |

OTHER PUBLICATIONS

English language Abstract of DE 19844261, 2000.
English language Abstract of DE 19933463, 2000.
English language Abstract of DE 19817292, 1999.
English language Abstract of DE 19929475, 2000.

* cited by examiner

*Primary Examiner* — Samira Jean-Louis

(74) *Attorney, Agent, or Firm* — Abel Law Group, LLP

(57) ABSTRACT

The present invention is a water-in-oil emulsion having a high content of water and relatively high amounts of skin-moisturizing agents and a cosmetic or dermatological stick including the water-in-oil emulsion. The present invention also includes methods of moisturizing the skin using the water-in-oil emulsion. The water-in-oil emulsion is solid at room temperature and comprises a fatty phase with at least one oil component and at least one wax component, an aqueous phase with a skin-moisturizing agent in addition to water, a water-in-oil emulsifier having the general structure A-B-A', where A' and A' represent the same or different hydrophobic inorganic groups and B is a hydrophilic group.

20 Claims, No Drawings

COSMETIC OR DERMATOLOGICAL STICK

CROSS-REFERENCE TO RELATED APPLICATIONS

This is a continuation application of PCT/EP02/10904, filed Sep. 27, 2002, which is incorporated herein by reference in its entirety, and also claims the benefit of German Application No. 101 48 314.7 filed Sep. 29, 2001, German Application No. 101 48 301.5 filed Sep. 29, 2001, German Application No. 101 48 302.3, filed Sep. 29, 2001, German Application No. 101 48 313.9, filed Sep. 29, 2001, German Application No. 101 50 619.8, filed Oct. 12, 2001, and German Application No. 101 55 960.7, filed Nov. 9, 2001.

FIELD OF THE INVENTION

The present invention is a water-in-oil emulsion having a high content of water and relatively high amounts of skin-moisturizing agents, and a cosmetic or dermatological stick including the water-in-oil emulsion. In particular, the present invention relates to sticks for the prophylaxis of wrinkles and antiwrinkle sticks, antiacne sticks, and sticks to combat blemished skin, sunscreen sticks and aftersun sticks, lipsticks, preferably lipcare sticks, but also decorative lipsticks, kohl pencils, foundation sticks, eyeshadow pencils, concealing sticks, eyebrow pencils, eyeliner pencils, and moisturizing sticks for the face and the body. These may additionally include photoprotective filters, pigments, powder substances, further active ingredients or repellents.

BACKGROUND OF THE INVENTION

Viewed technically, most stick formulations are anhydrous fatty mixtures of solid or semi-solid waxes and liquid oils, where the highly purified paraffin oils and waxes represent the lipstick base mass. Water-containing preparations are also known, which are also sometimes in the form of water-in-oil emulsions.

Customary base substances of the prior art for stick-like preparations are, for example, liquid oils (e.g. paraffin oils, castor oil, isopropyl myristate), semi-solid constituents (e.g. Vaseline, lanolin), solid constituents (e.g. beeswax, ceresin and microcrystalline waxes or ozokerite), and high-melting waxes (e.g. carnauba wax, candelilla wax).

The disadvantage of sticks for face and cheeks known hitherto is firstly the inadequate stability of the sticks. Many sticks are sensitive to shear forces, and crumble easily, meaning that the decorative emulsion cannot be distributed on the skin very easily. In addition, they are not particularly temperature-stable, smear and run upon use in the hot summer months, while in winter at cold temperatures they become brittle and dull.

Also, the sensory properties have hitherto left something to be desired. The sticks should actually have a pleasant cooling effect on the skin and feel creamy, which is only achieved in part with the products according to the prior art.

Standard commercial antiwrinkle products are in most cases lotions, creams, gel creams, which have a content of active ingredients for reducing the wrinkling of skin. It would be desirable to be able to apply these active ingredients in a targeted manner to the affected areas of the skin. Suitable for this purpose are stick formulations, although currently these are known in the market only in the form of lipcare sticks, foundation sticks and the like, and are not conceived for the reduction or prophylaxis of wrinkles. Such sticks would be advantageous since they could be applied in a targeted manner to areas around the corners of the mouth or in the eye and forehead area. In addition, it can be expected that the applied stick ingredients spread to a lesser degree on the skin, which could be advantageous particularly in the eye area.

Even when pressed lightly, a cosmetic stick should give them a nongreasy, dull or sticky, but nevertheless well-adhering fatty film. This fatty film then makes the lips or the skin smooth and supple.

The skin of the lips has only an extremely thin horny layer. There are no sweat glands on the lips, and only a few sebaceous glands. The skin on the lips is therefore virtually free from lipids and is prone to drying out, particularly in cold and dry weather. It is possible for small cracks to form in the skin, and the susceptibility of the lips to chemical, physical and microbial effects (e.g. of foods, sunlight, Herpes simplex viruses) increases.

The aim of lipcare sticks is to prevent this. These products usually contain a high content of waxes and fatty components which form a covering layer over the lips following application.

The preparations for lipcare sticks can additionally have incorporated into them active ingredients which are required for lipcare or lip protection, for example vitamins, moisturizing agents, photoprotective agents, concealing pigments etc.

The dermis of the lips has papillae which have a good blood supply and extend up to just under the surface of the lips. For this reason, the lips are reddish in color and, depending on the coloring of the person in question, distinguished from the other facial skin in terms of color to a greater or lesser degree. A styling means of decorative cosmetics is then also to match the lip color to the type of person through appropriate cosmetics.

Products of this type are decorative lipsticks into which a very wide variety of color pigments can be incorporated. These sticks too comprise high contents of waxes and fatty components which form a covering lipid layer over the lips following application.

However, the object of this layer is not primarily to protect the lip skin from drying out. The lipid layer here serves as a base for the incorporated pigment substances which adheres to the lips; the pigments themselves cannot be applied to the lips without such a base for many reasons.

It is also possible to combine the properties of care and decorative lipsticks together, i.e. to incorporate care or protecting substances into decorative lipsticks.

Acne is a skin disorder with various forms and causes, characterized by uninflamed and inflamed bumps, originating from blocked hair follicles (comedones) which can lead to the formation of pustules, abscesses and scars. The most frequent form is Acne vulgaris, which occurs primarily in puberty. Causative conditions of Acne vulgaris are the keratinization and blocking of the hair follicle opening, the production of sebum, which is dependent on the level of male sex hormones in the blood, and the production of free fatty acids and tissue-damaging enzymes by bacteria (*Propionibacterium acnes*).

Antiacne active ingredients such as octoxyglycerol are described, for example, in U.S. Pat. No. 6,040,347 and DE 4240674. Although sticks are also mentioned there as a conceivable application form, anhydrous fatty sticks are to be understood by this. The advantages of formulating the active ingredient in a water-containing W/O stick was not recognized.

Lipcare sticks in most cases comprise a high content of waxes and fatty components which, following application, form a covering layer over the lips. The preparations for lipcare sticks can additionally have incorporated into them active ingredients which are required for lipcare or lip protection, for example vitamins, moisturizing agents, photoprotective agents, concealing pigments etc.

Lipsticks of the prior art with a content of paraffins and beeswax are described in "Kosmetik, Entwicklung Herstellung und Anwendung kosmetischer Mittel" [Cosmetics, development, preparation and use of cosmetic compositions], p. 105, Editor: W. Umbach, Georg Thieme Verlag, Stuttgart—New York, 1988.

Since both care and also primarily decorative lipsticks of the prior art have in some instances serious shortcomings, an object of the present invention was to overcome these shortcomings.

Due to the high sensitivity of the lip area, in particular toward ultraviolet radiation as a consequence of the virtually complete lack of pigments, it is advisable, especially in cases of increased UV exposure, such as in high mountains, to provide the lip area with protection against UV radiation in the form of corresponding stick-like photoprotective preparations. Inorganic pigments are often used particularly in stick-like preparations of the prior art as UV absorbers or UV reflectors for protecting the lip area against UV rays. These are, in particular, oxides of titanium, but also sometimes of zinc, iron, zirconium, silicon, manganese, aluminum, cerium and mixtures thereof, and also modifications.

A considerable shortcoming of the formulations of the prior art is, inter alia, that, due to the low water contents of per se acceptable emulsion sticks, it is virtually impossible to incorporate water-soluble UV filter substances into such formulations. It was thus a further object of the present invention to make available sticks with exclusively water-soluble UV filters or water-dispersible pigments (for example titanium dioxide), or combinations of water-soluble and fat-soluble UV filters and pigments.

The prior art has other disadvantages. These include the fact that water-soluble active ingredients are often not sufficiently fat-soluble to be incorporated into the cosmetic bases to a noteworthy degree. On the other hand, a certain water content would be entirely desired in order to increase the compatibility of the cosmetic stick with the human skin. In addition, it is therefore not possible to make sticks with very high water contents in accordance with the prior art because the water is incompatible with the hydrophobic oil/wax/emulsifier matrix.

Sticks which, besides relatively large amounts of water, additionally comprise relatively large concentrations of water-soluble active ingredients, high concentrations of skin-moisturizing agents (3-50% of glycerol, for example) and of fat-soluble active ingredients are not described. Although sticks with relatively large amounts of water are known, active moisturizing of the skin, which should, in addition, last for a relatively long time and have biophysically measurable moisturizing values like a classic O/W or W/O emulsion is unknown. This is probably due to the fact that only extremely short-term moisturizing is brought about by water. In addition, low-water or anhydrous stick formulations are only therefore passively moisturizing because occlusive waxes are used which cause a build-up of water in the skin. Active moisturizing by a hydrolipid film comprising water which additionally comprises relatively large amounts of skin-moisturizing agents instead of an occlusive lipid film or of an only water-containing stick has hitherto not been described as advantageous. However, such sunscreen or aftersun sticks would be advantageous since active ingredient-containing hydrolipid films could then form instead of lipid films. In addition, the waxes used could additionally cause occlusive effects, as in the case of anhydrous sticks, resulting in a synergism from water, moisturizing agent and wax for emulsion sticks designed in this way.

In addition, it was hitherto not known that water-containing sticks can additionally comprise concealing pigments, or else combinations of concealing pigments and pearlescent pigments or exclusively pearlescent pigments. Pearlescent pigments are, for example, therefore difficult to integrate into water-containing formulations because they are shear-sensitive, meaning that the pearlescent effect fails to appear or only unstable formulations arise. In addition, the pigments used generally have to be made compatible with the water/moisturizing agent/lipid/wax matrix.

According to the ideal profile of requirements, cosmetic or dermatological sticks should be able to be applied smoothly and without great friction resistance. Moreover, such a formulation must also satisfy the requirements that the stick in question must be fracture-resistant and temperature-resistant and the formulation must not lose oil.

If cosmetic or pharmaceutical sticks are to contain certain active ingredients, it is conceivable that the other constituents are incompatible with the active ingredients. This is the case particularly frequently when the cosmetic sticks are intended to be used as sunscreen sticks or aftersun sticks, when water-soluble photoprotective filters are to be present in the stick in relatively large amounts, when, for the preparation of a prophylactic antiwrinkle stick or of an antiwrinkle stick, water-soluble active ingredients are to be incorporated in amounts known to the person skilled in the art, when, for the preparation of an antiacne stick, water-soluble antiacne active ingredients are to be incorporated in amounts known to the person skilled in the art, when water-soluble skin-moisturizing agents are to be present in the stick in relatively large amounts or when, for the preparation of a stick, further fat- or water-soluble active ingredients, such as pigments, pearlescent pigments, vitamins and/or antioxidants, are to be additionally incorporated.

For an antiacne stick, for example, it would, however, be particularly advantageous if the content of fat-soluble constituents were as low as possible.

Pearlescent pigments are difficult to integrate into water-containing formulations because they are shear-sensitive, meaning that the pearlescent effect fails to appear or only unstable formulations arise. In addition, the pigments used generally have to be made compatible with the water/moisturizing agent/lipid/wax matrix.

Admittedly, both WO 98/17232 and EP 1 064 908 describe cosmetic and dermatological sticks with a high water content where, in the former, the emulsifier system according to the invention is also described and, in the latter, the use of pigments.

The most important ingredient of a stick is the pigments, which have to be stably incorporated into the system and represent the color-imparting component. The incorporation of pigments into emulsion sticks may result in various instabilities. In mild cases, these are color inhomogeneities, where the different pigments are not distributed evenly within the stick. In more serious cases, instabilities in the stick system may arise where temperature stability and stability to breaking are impaired.

For this reason, it is important for an appealing stick (sensorally attractive, optically flawless and stable) that all of the components of the system are matched to one another.

This includes both the combination of the pigments and fillers and suitable selection of emulsifiers, waxes and oils.

The specifications cited above were unable to point the way to the present invention since the sticks mentioned therein are not sticks (foundation sticks) whose contents are applied over a large area on the face. The stability of the sticks according to the invention is also far superior to that of those described hitherto. They are considerably less sensitive to shear forces and remain stable and spreadable within the entire temperature range from −10° C. to 53° C. Above all, the sensory properties of the sticks according to the invention differ from those which are disclosed in the specifications cited above.

DE 23 35 549 discloses a process for the preparation of a cosmetic stick based on a W/O emulsion. According to this teaching, a gel is prepared from a polyhydroxy compound and a nonionogenic, surface-active compound; this is mixed with a cosmetic base, and water is emulsified into the mixture.

DE 41 28 748 describes cosmetic sticks which are characterized in that they represent emulsions and comprise, as essential constituents, beeswax, one or more esters of a saturated carboxylic acid having 20-40 carbon atoms and a saturated alcohol having 14-34 carbon atoms, water, and optionally further lipids and/or customary auxiliaries and additives.

U.S. Pat. No. 4,719,103 describes an antiperspirant stick based on a W/O emulsion which has a high water content, which is characterized by a content of volatile silicone components, a solid alkanol, and polyglycerol fatty acid esters, for example polyglyceryl isostearate, as emulsifier. U.S. Pat. No. 4,704,271 and U.S. Pat. No. 4,725,431 describe similar preparations.

EP 0748622 describes sticks containing volatile oils, water-repelling polymers which are soluble in the volatile oil, and nonvolatile oils and powder ingredients.

GB 2162439 describes paraffin-containing sticks which reportedly have a high water content, the emulsifier being chosen from the group of metal salts.

DE 19643237 describes cosmetic sticks which are characterized by a relatively high water content. These comprise, inter alia, certain wax and oil components, certain W/O emulsifiers, besides 30 to 85% by weight of water. The use of relatively large amounts of skin-moisturizing agents is not described, only the use of 2% by weight of glycerol is disclosed in the examples.

DE 29919474 describes W/O emulsion sticks. By using polysaccharides, a three-dimensional structure is produced which reportedly confers more stability to the sticks. The use of large amounts of skin-moisturizing agents also in the presence of pigments is not described. Also, the omission of polysaccharides while retaining the stick structure is not regarded as being advantageous.

DE 20009445 claims sticks which comprise only small amounts of water (25%). Nothing is stated concerning skin-moisturizing agents.

EP 1064908 describes emulsion sticks which comprise only very small water contents (14%, p. 4, Ex. 3). The content of skin-moisturizing agents is 9% (glycerol, butylene glycol, sorbitol). For the use in antiacne products in particular, a particularly low content of oils or lipids would, by contrast, be advantageous since these counteract the healing of the acne.

EP 0194887 describes the use of ethoxylated waxes and also triglyceride waxes for the preparation of anhydrous sticks.

WO 9817232 and describe lipsticks which are characterized by a relatively high content of water. Since besides the described cooling effect, the substantivity (for example upon use of colored pigments or pearlescent pigments) for certain sticks, which additionally reportedly comprise relatively large amounts of skin-moisturizing agents, is also important, it was discussed further in the specification.

This has also not been explained in the invention which is described above. In addition, it has hitherto not been mentioned that cosmetic sticks can also be prepared in the presence of triglyceride waxes or ethoxylated waxes.

A considerable shortcoming of the formulations of the prior art is, inter alia, that, due to the low water contents of perfectly acceptable emulsion sticks, it was virtually impossible to incorporate water-soluble antiacne active ingredients into such formulations. For example, water-soluble or dispersible active ingredients, such as lactic acid, salicylic acid, short-chain mono-, di- and triglycerol esters (C8-12 fatty acids), aluminum salts, glycerol ethers, zinc compounds, alkyl-branched fatty acids, can only be incorporated with difficulty as antiacne active ingredients in accordance with the prior art.

A considerable shortcoming of the formulations of the prior art is, inter alia, that, due to the low water contents of per se acceptable emulsion sticks, it was virtually impossible to incorporate water-soluble antiwrinkle active ingredients into such formulations. In addition, there is a shortcoming in combining water-soluble or fat-soluble active ingredients. For example, water-soluble or dispersible active ingredients, such as vitamin C, carnitine, lipoic acid, alpha-hydroxy acids, can only be incorporated with difficulty as antiwrinkle active ingredients in accordance with the prior art.

Pearlescent pigments are difficult to integrate into water-containing formulations because they are shear-sensitive, meaning that the pearlescent effect fails to appear or only unstable formulations arise. In addition, the pigments used generally have to be made compatible with the water/moisturizing agent/lipid/wax matrix.

SUMMARY OF THE INVENTION

Starting from this, the object of the invention is to formulate solid W/O emulsions such that, besides a high water content, a high content of skin-moisturizing agents can be stabily incorporated. In addition, it should also be possible to stabily incorporate antiacne active ingredients; water-soluble antiwrinkle active ingredients or combinations of water-soluble and fat-soluble antiwrinkle active ingredients; solids such as pigments, powder substances and UV filters; water-soluble or water-dispersible active ingredients; and lipid-soluble or lipid-dispersible active ingredients, in particular antioxidants, UV filters and repellents, into the solid W/O emulsions.

After all this, it was surprising and could not have been foreseen that W/O emulsions, which are solid at room temperature, comprising
  (a) a fatty phase which includes
    (a1) at least one oil component
    (a2) at least one wax component,
  (b) a water phase which includes
    (b1) 30 to 85% by weight of water and
    (b2) 5 to 50% by weight of a skin-moisturizing agent selected from the group consisting of glycerol, chitosan, Fucogel, propylene glycol, polyethylene glycol, dipropylene glycol, butylene glycol, mannitol, lactic acid, polyethylene glycol, glycine, sodium pyrrolidonecarboxylic acid, hyaluronic acid, salts of the given acids, and urea and salts of metals of the first and second main group,
  (c) a W/O emulsifier or a mixture of two or more W/O emulsifiers chosen from the group of interface-active substances of the general structure A-B-A', where A and A' are identical or different hydrophobic organic radicals, and B is a hydrophilic group,
would overcome the disadvantages of the prior art.

DETAILED DESCRIPTION OF THE PREFERRED EMBODIMENTS

Here, it is preferred when the W/O emulsifier or the W/O emulsifiers are chosen from the group of substances of the general formula

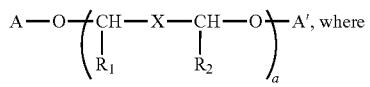

A and A' are identical or different hydrophobic organic radicals, a is a number from 1 to 100, preferably 2 to 60, in particular 5 to 40, X is a single bond or the group

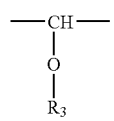

$R_1$ and $R_2$, independently of one another, are H, methyl, but chosen such that those radicals are not methyl at the same time, $R_3$ is chosen from the group consisting of H, and branched and unbranched, saturated and unsaturated alkyl and acyl radicals having 1-20 carbon atoms, or that the W/O emulsifier or emulsifiers are chosen from the group of fatty alcohols having 8-30 carbon atoms, monoglycerol esters of saturated or unsaturated, branched or unbranched alkanecarboxylic acids or hydroxyalkanoic acids with a chain length of 8-24, in particular 12-18, carbon atoms, diglycerol esters of saturated or unsaturated, branched or unbranched alkanecarboxylic acids or hydroxyalkanoic acids with a chain length of 8-24, in particular 12-18, carbon atoms, triglycerol esters of saturated or unsaturated, branched or unbranched alkanecarboxylic acids or hydroxyalkanoic acids with a chain length of 8-24, in particular 12-18, carbon atoms, polyglycerol esters of saturated or unsaturated, branched or unbranched alkanecarboxylic acids or hydroxyalkanoic acids with a chain length of 8-24, in particular 12-18, carbon atoms with up to 10 glycerol units, monoglycerol ethers of saturated or unsaturated, branched or unbranched alcohols with a chain length of 8-24, in particular 12-18, carbon atoms, diglycerol ethers of saturated or unsaturated, branched or unbranched alcohols with a chain length of 8-24, in particular 12-18, carbon atoms, triglycerol ethers of saturated or unsaturated, branched or unbranched alcohols with a chain length of 8-24, in particular 12-18, carbon atoms, polyglycerol ethers of saturated or unsaturated, branched or unbranched alcohols with a chain length of 8-24, in particular 12-18, carbon atoms, with up to 10 glycerol units, propylene glycol esters of saturated or unsaturated, branched or unbranched alkanecarboxylic acids or hydroxyalkanoic acids with a chain length of 8-24, in particular 12-18, carbon atoms, sorbitan esters of saturated or unsaturated, branched or unbranched alkanecarboxylic acids or hydroxyalkanoic acids with a chain length of 8-24, in particular 12-18, carbon atoms, sorbitan esters of polyols, in particular of glycerol, pentaerythrityl esters of saturated or unsaturated, branched or unbranched alkanecarboxylic acids or hydroxyalkanoic acids with a chain length of 8-24, in particular 12-18, carbon atoms, methylglucose esters of saturated or unsaturated, branched or unbranched alkanecarboxylic acids or hydroxyalkanoic acids with a chain length of 8-24, in particular 12-18, carbon atoms, polyglycerol methylglucose esters of saturated or unsaturated, branched or unbranched alkanecarboxylic acids or hydroxyalkanoic acids with a chain length of 8-24, in particular 12-18, carbon atoms, of glyceryl fatty acid citrates, cetyl dimethicone copolyols, of alkyl methicone copolyols, of alkyl dimethicone ethoxyglucosides, or that the abovementioned types of W/O emulsifiers have been additionally polyethoxylated and/or polypropoxylated in such a way that they represent ethoxylated and/or propoxylated W/O emulsifiers.

It is particularly preferred when the W/O emulsifier or the W/O emulsifiers are chosen such that the radicals A and A' are advantageously chosen from the group of branched and unbranched, saturated and unsaturated alkyl and acyl radicals and hydroxyacyl radicals having 10-30 carbon atoms, and also from the group of hydroxyacyl groups joined together via ester functions, according to the scheme

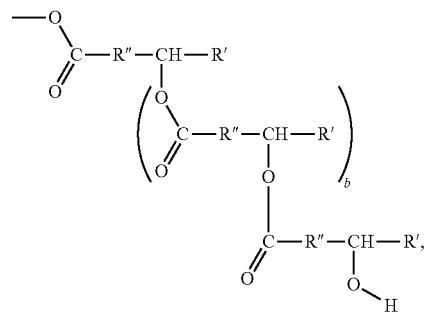

where R' is chosen from the group of branched and unbranched alkyl groups having 1 to 20 carbon atoms and R" is chosen from the group of branched and unbranched alkylene groups having 1 to 20 carbon atoms, and b can assume numbers from 0 to 200.

It is very particularly preferred when the W/O emulsifier or emulsifiers are chosen from the group consisting of PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methylglucose distearate, steareth-2.

It is preferred when the stabilizer or stabilizers is chosen from the group of substances of the general formula

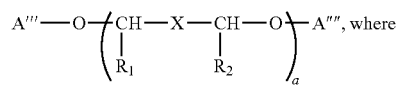

A''' and A'''' are identical or different hydrophobic organic radicals, a is a number from 1 to 100, preferably 2 to 60, X is a single bond or the group

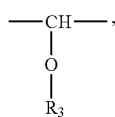

$R_1$ and $R_2$, independently of one another, are chosen from the group consisting of H, methyl, but such that both radicals are not methyl at the same time, $R_3$ is chosen from the group consisting of H, and branched and unbranched, saturated and unsaturated alkyl and acyl radicals having 1-20 carbon atoms, where the radicals A''' and A'''' may be identical or different and are chosen from the group

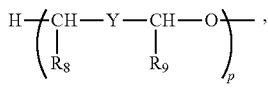

where $R_8$ and $R_9$ may be identical or different and are chosen from the group of saturated and unsaturated alkyl and acyl radicals having 1-30 carbon atoms, p is a number from 1-20, and Y is a single bond or the group

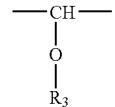

where $R_3$ is chosen from the group consisting of H, and branched and unbranched, saturated and unsaturated alkyl and acyl radicals having 1-30 carbon atoms, in addition the group A''' and A'''' may, independently of one another, also be alkyl radicals or acyl radicals.

It is particularly preferred when the stabilizer used is the PEG-45/dodecyl glycol copolymer, the PEG-22/dodecyl glycol copolymer and/or the methoxy PEG-22/dodecyl glycol copolymer.

It is particularly preferred when the W/O emulsion according to the invention is solid at room temperature.

Preference is given to a cosmetic or dermatological stick comprising emulsions according to the invention which is spreadable and storage-stable in a temperature range from −10° C. to 50° C.

Particularly preferably, the stick according to the invention is supplied in a sleeve-like packaging. In this connection, the stick sleeve can particularly preferably be filled on both sides from top and bottom. The stick sleeve can very particularly preferably be filled at a temperature of 90° C.

In addition, it is preferred when the oil component or the totality of the oil components is chosen from the group of esters of saturated or unsaturated, branched or unbranched alkanecarboxylic acids with a chain length of from 1 to 44 carbon atoms and saturated or unsaturated, branched or unbranched alcohols with a chain length of from 1 to 44 carbon atoms, from the group of esters of aromatic carboxylic acids and saturated or unsaturated, branched or unbranched alcohols with a chain length of from 1 to 30 carbon atoms, provided the oil component or the totality of the oil components represent a liquid at room temperature.

It is particularly preferred when the oil component or the totality of the oil components is chosen from the group of branched and unbranched hydrocarbons, of silicone oils, lanolins, of adipic esters, of butylene glycol diesters, of dialkyl ethers or carbonates, the group of saturated or unsaturated, branched alcohols, and the fatty acid triglycerides, namely the triglycerol esters of saturated or unsaturated, branched or unbranched alkanecarboxylic acids with a chain length of from 8 to 24, in particular 12-18, carbon atoms, where the triglycerol esters are preferably chosen from the group of synthetic, semisynthetic and natural oils, such as olive oil, sunflower oil, soybean oil, peanut oil, rapeseed oil, almond oil, palm oil, coconut oil, and palm kernel oil.

In addition, it is preferred when the wax component or the totality of the wax components is chosen from the group
- of esters of saturated or unsaturated, branched or unbranched alkanecarboxylic acids with a chain length of from 1 to 80 carbon atoms, and saturated or unsaturated, branched or unbranched alcohols with a chain length of from 1 to 80 carbon atoms, from the group of esters of aromatic carboxylic acids and saturated or unsaturated, branched or unbranched alcohols with a chain length of from 1 to 80 carbon atoms provided the wax component or the totality of the wax components represent a solid at room temperature,
- of natural waxes,
- of diesters of polyols and C10-C80 fatty acids,
- of ethoxylated waxes,
- of triglyceride waxes,
- of C16-C60 fatty acids (or the salts thereof) and C16-C80 fatty alcohols.

It is particularly preferred when the wax component or the totality of the wax components is chosen from the group
- of esters of saturated branched alkanecarboxylic acids with a chain length of from 1 to 44 carbon atoms and saturated branched alcohols with a chain length of from 1 to 44 carbon atoms, provided the wax component or the totality of the wax components represent a solid at room temperature,
- of natural waxes,
- of diesters of polyols and C10-C80 fatty acids,
- of ethoxylated waxes,
- of triglyceride waxes,
- of C16-C60 fatty acids (or salts thereof) and C16-C80 fatty alcohols.

It is also preferred when a content of one or more water-soluble or water-swellable polymers is additionally present, in particular cellulose or starch derivatives etherified with alkyl groups, preferably β-glucans, xanthan gum, dextrans, hydroxymethylcellulose, hydroxyethylcellulose or hydroxypropylcellulose, methoxy-PEG-22/dodecyl glycol copolymers, poloxamers, hydrophilic starch esterified with one or more n-octenyl succinate radicals.

The described W/O emulsions are particularly suitable as cosmetic or dermatological preparations for the treatment of acne disorders of the skin, for the prevention or treatment of damage to the skin caused by UV light, and for decoration of the skin.

In this connection, it is preferred to prepare the emulsions in the form of sticks.

In addition, it is preferred when emulsions or sticks according to the invention additionally comprise
(a) at least one pigment, at least one dye or at least one powder substance,
(b) at least one antiwrinkle substance,
(c) at least one UVA filter substance, at least one UVB filter substance or at least one inorganic pigment, or
(d) at least one antiacne substance.

The invention also covers the use of emulsions or sticks according to the invention for moisturizing the skin.

In the case of a content of at least one pigment, at least one dye or at least one powder substance, it is preferred that coated pigments are used as pigments.

In the case of a content of at least one pigment, at least one dye or at least one powder substance, it is preferred when emulsions or sticks according to the invention additionally comprise fillers and the total amount of pigments and fillers is 10 to 20% by weight of the preparation, where the aqueous phase is particularly preferably present in a concentration from 35 to 75% by weight.

In the case of a content of at least one pigment, at least one dye or at least one powder substance, it is preferred when the oil component or the totality of the oil components is chosen from the group of branched and unbranched hydrocarbons, lanolins, adipic esters, butylene glycol diesters, cyclic or linear silicone oils, branched and unbranched salicylates and benzoates, dialkyl ethers, dialkyl carbonates, saturated and unsaturated, branched alcohols, and fatty acid triglycerides, namely the synthetic or natural triglycerol esters of saturated or unsaturated, branched or unbranched alkanecarboxylic acids with a chain length of from 8 to 24, in particular 12 to 18, carbon atoms.

In the case of a content of at least one pigment, at least one dye or at least one powder substance, it is preferred that ester waxes are used as waxes.

Such emulsions or sticks with a content of at least one pigment, at least one dye or at least one powder substance are preferably used as cosmetic preparations, for the decoration of the skin or as make-up for face and cheeks (foundation) which can be applied evenly and have a cooling and care effect.

In the case of a content of at least one UVA filter substance, at least one UVB filter substance or at least one inorganic pigment, it is preferred when the sticks or emulsions according to the invention comprise further UV filters from the group of benzotriazoles, triazines, hydroxybenzophenone derivatives, water-soluble, sulfonated and organic or inorganic pigments which are liquid at room temperature.

In the case of a content of at least one UVA filter substance, at least one UVB filter substance or at least one inorganic pigment, it is particularly preferred that the hydroxybenzophenone used is a hydroxybenzophenone having a chemical structure of formula

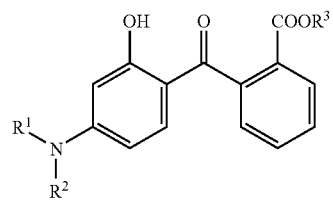

in which
$R^1$ and $R^2$, independently of one another, are hydrogen, $C_1$-$C_{20}$-alkyl, $C_3$-$C_{10}$-cycloalkyl or $C_3$-$C_{10}$-cycloalkenyl, where the substituents $R^1$ and $R^2$, together with the nitrogen atom to which they are bonded, can form a 5-membered or 6-membered ring, and $R^3$ is a $C_1$-$C_{20}$-alkyl radical.

In the case of a content of at least one UVA filter substance, at least one UVB filter substance or at least one inorganic pigment, it is very particularly preferred for the emulsions or sticks according to the invention that the hydroxybenzophenone chosen is aminobenzophenone, which is characterized by the chemical structure of formula

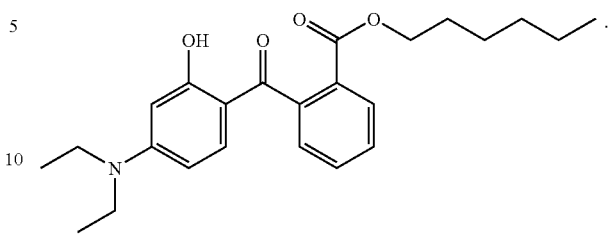

In the case of a content of at least one UVA filter substance, at least one UVB filter substance or at least one inorganic pigment, it is very extraordinarily preferred that emulsions or sticks according to the invention comprise further UV filters from the group of benzotriazoles, triazines, water-soluble, sulfonated and organic or inorganic pigments which are liquid at room temperature.

In the case of a content of at least one UVA filter substance, at least one UVB filter substance or at least one inorganic pigment, it is particularly preferred that the oil component or the totality of the oil components is chosen from the group of branched and unbranched hydrocarbons, lanolins, adipic esters, butylene glycol diesters of cyclic or linear silicone oils, dialkyl ethers, dialkyl carbonates, saturated or unsaturated, branched alcohols, and fatty acid triglycerides, particularly preferably the synthetic or natural triglycerol esters of saturated or unsaturated, branched or unbranched alkanecarboxylic acids with a chain length of from 8 to 24, particularly preferably 12 to 18, carbon atoms, of branched and unbranched salicylates and benzoates.

In the case of a content of at least one antiacne substance, the W/O emulsifiers used may advantageously be glyceryl fatty acid citrates in addition to the abovementioned preferred emulsifiers.

It was surprising that the preparations according to the invention permit the incorporation of large amounts of water, even in the presence of only small amounts of emulsifiers used according to the invention. The release of, in particular, water-soluble active ingredients is significantly increased compared with conventional preparations. One example is the increase in the sun protection factor: photoprotective agents incorporated into the formulation according to the invention are more effective in a lower concentration than the preparations of the prior art, thus, for example, compared with W/O sticks with a low water content or compared with anhydrous suspension sticks. The release of, in particular, water-soluble active ingredients is significantly increased compared with conventional preparations. Antiacne active ingredients incorporated into the formulation according to the invention are more effective in a lower concentration than the preparations of the prior art, thus, for example, compared with W/O sticks with a low water content or compared with anhydrous suspension sticks. It can be shown that skin moisturization values result which are usually only known from flowable O/W or W/O emulsions (Nivea). In addition, it is possible to incorporate pigments, powder raw materials or even pearlescent pigments in the presence of relatively high concentrations of water and moisturizing agent. It was surprising that the adhesion of such stick formulations is excellent, a cooling effect results, and the products are nonsticky. This was notable in as much as since through the use of relatively large contents of water and relatively large concentrations of moisturizing agents (3-60%), essentially fewer adhering ingredients, such as oil components and waxes, is available per rubbed-off amount of stick compared with anhydrous sticks or sticks only containing water. In addition, such colored sticks likewise have very good moisturizing properties and therefore differ from customary commercial products whose moisturizing effect is caused only by occlusion. The water phase in such sticks has several advantages: it produces a cooling effect, is a medium for dissolving the skin-moisturizing agent, permits the dissolution of water-soluble active ingredients, gives the stick pleasant sensory properties and allows more cost-effective formulations compared with pure fatty sticks to be offered. Furthermore, additionally incorporated pigments also lead to a wrinkle-concealing effect.

It was surprising that emulsion sticks according to the invention which maintain SPF values of 25 or above can be prepared in the presence of relatively large concentrations of skin-moisturizing agents. Sticks with high SPF values which simultaneously cool the skin and additionally release skin-moisturizing agents or active ingredients to the skin are particularly elegant. High SPF values could also be realized through the combined use of water-soluble and fat-soluble UV filters, where additionally titanium dioxide is also advantageous as pigment. This combined use of water-soluble and fat-soluble UV filters is facilitated compared with pure fatty sticks because a water phase is additionally present in the solid W/O sticks, which first makes it possible for the water-soluble filter to dissolve and thus permits a synergism. This is true analogously for pigments which are dispersible in water. The water phase in such sticks therefore has several advantages: it produces a cooling effect, is a medium for dissolving the skin-moisturizing agent, permits the dissolution of water-soluble filters and pigments and further water-soluble active ingredients, gives the stick pleasant sensory properties and allows more cost-effective formulations compared with pure fatty sticks to be offered.

However, the cosmetic properties of the water-rich sticks according to the invention also prove to be significantly improved compared with those of the prior art. For example, even without further additions, it is possible to achieve a pleasant cooling effect on the skin through mere application, which is pleasantly noticeable in particular in the case of use as a lipcare stick, decorative lipstick, kohl pencil, foundation stick, eye shadow pencil, concealing stick, lipstick with sunscreen filters, eyebrow pencil, eyeliner pencil, moisturizing stick for the face or body, prophylactic antiwrinkle stick, antiwrinkle stick, sunscreen stick, repellent stick or aftersun stick. Aftersun sticks which can be formulated with or without UV filters in the presence of active ingredients which alleviate the sunburn subsequently or prophylactically are advantageous due to the cooling effect upon application to skin damaged by sunburn.

In the case of use as decorative lipsticks, kohl pencils, foundation sticks, eye shadow sticks, concealing sticks, eyebrow pencils, eyeliner pencils, moisturizing stick for the face or body, sticks with a content of antiwrinkle substances, sunscreen sticks, repellent sticks and aftersun sticks, significant improvements are noticeable compared with the prior art by virtue of the fact that, for example, for the preparation of these sticks it is possible to use water-dispersible titanium dioxide, or else combinations of lipid-dispersible and water-dispersible metal oxides.

The invention also provides the process for the preparation of emulsions according to the invention. The preparation of sticks according to the invention is very simple since it is a one-step process in which, for example, the water phase is added to the hot fatty phase and then cooled to room temperature.

In addition, the process according to the invention is characterized by the fact that it is possible to use a large number of emulsifiers or oil components for the preparation of the sticks according to the invention.

The preparation of sticks according to the invention is very simple since it is a one-step process in which, for example, the water phase is added to the hot fatty phase and then cooled to room temperature.

The cosmetic or dermatological stick according to the invention is, according to the invention, advantageously packaged in a stick sleeve which can be filled on both sides from top and bottom. This stick sleeve can be filled at a pouring temperature of 90° C. Such stick sleeves are supplied, for example, by Laffon.

In addition, a stick sleeve for cosmetic or dermatological preparations comprising a cosmetic make-up preparation as is described in this specification is in accordance with the invention.

Last but not least, the use of a stick according to the invention as a make-up stick for face and cheeks (foundation) which can be applied evenly and has a cooling and care effect is in accordance with the invention.

Surprisingly, it has been found that the water-soluble and water-swellable polymers used according to the invention moreover increase the skin-friendliness of the cosmetic preparations according to the invention. A more pleasant feel is achieved upon applying the stick mass to the skin.

The oil component or the totality of the oil components of the water-containing, cosmetic sticks according to the invention should be a liquid at room temperature and the wax component or the totality of the wax components should form a solid at room temperature. It is advantageous to match the oil components and the wax components to one another such that the mixture of oil components and wax components without remaining components, i.e. for example without water phase and without emulsifier, forms a solid at room temperature.

The oil component or the totality of the oil components of the water-containing, cosmetic sticks according to the invention is preferably chosen from the group of esters of saturated or unsaturated, branched or unbranched alkanecarboxylic acids with a chain length of from 1 to 44 carbon atoms, saturated or unsaturated, branched or unbranched alcohols with a chain length of from 1 to 44 carbon atoms, from the group of esters of aromatic carboxylic acids and saturated or unsaturated, branched or unbranched alcohols with a chain length of from 1 to 30 carbon atoms provided the oil component or the totality of the oil components are liquid at room temperature. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the oil phase can advantageously be chosen from the group of branched and unbranched hydrocarbons, silicone oils, lanolins, adipic esters, butylene glycol diesters, dialkyl ethers or carbonates, saturated or unsaturated, branched alcohols, and fatty acid triglycerides, namely the triglycerol esters of saturated or unsaturated, branched or unbranched alkanecarboxylic acids with a chain length of from 8 to 24, in particular 12 to 18, carbon atoms. The fatty acid triglycerides can, for example, advantageously be chosen from the group of synthetic, semisynthetic and natural oils, e.g. olive oil, sunflower oil, soybean oil, peanut oil, rapeseed oil, almond oil, palm oil, coconut oil, palm kernel oil, castor oil, wheat germ oil, grape seed oil, thistle oil, evening primrose oil, macadamian nut oil and the like. Of importance according to the invention are, for example, cocoglycerides (Myritol 331).

Advantageously, the oil phase can also have a content of cyclic or linear silicone oils or consist entirely of such oils, although it is preferred to use an additional content of other oil phase components apart from the silicone oil or the silicone oils. Advantageous oil components are also, for example, butyloctyl salicylate (for example that available under the trade name Hallbrite BHB from CP Hall), hexadecyl benzoate and butyloctyl benzoate and mixtures thereof, (Hallstar AB) and/or diethylhexyl naphthalate (Hallbrite TQ).

Cyclomethicone (octamethylcyclotetrasiloxane) is advantageously used as the silicone oil according to the invention. However, other silicone oils are also to be used advantageously for the purposes of the present invention, for example hexamethylcyclotrisiloxane, polydimethylsiloxane and poly(methylphenylsiloxane).

Very particularly advantageous oil components can be chosen from the group consisting of ethylhexyl cocoate, myristyl myristate, dicaprylyl carbonate, cetearyl isononanoate, octyldodecanol, polydecenes, squalane, dicaprylyl ether, triisostearine, butylene glycol dicaprylate/dicaprate, castor oil, caprylic/capric triglyceride, di(2-ethylhexyl) adipate, lanolin oil, isopropyl palmitate and cocoglyceride. In addition, natural oils, such as avocado oil and macadamia oil are also particularly advantageous. Of these, dicaprylyl carbonate, cetearyl isononanoate, octyidodecanol, caprylic/capric triglyceride, di(2-ethylhexyl) adipate, avocado oil and *macadamia* oil are of particularly excellent advantage.

The oil phase is particularly advantageously chosen from the group consisting of dicaprylyl carbonate, octyldodecanol, dicaprylyl ether, ethylhexyl cocoate, caprylic/capric triglyceride, di(2-ethylhexyl) adipate, cocoglyceride, butyloctyl salicylate, hexyldecyl benzoate, butyloctyl benzoate, C12-15 alkyl benzoate, lanolin oil, butylene glycol dicaprylate/dicaprate and cetearyl isononanoate.

In the case of a content of at least one pigment, at least one dye or at least one powder substance, lipids are also preferably chosen from the group of synthetic and natural esters of saturated or unsaturated, branched or unbranched alkanecarboxylic acids with a chain length of from 3 to 30 carbon atoms and saturated or unsaturated, branched or unbranched alcohols with a chain length of from 3 to 30 carbon atoms, and also from the group of esters of aromatic carboxylic acids and saturated or unsaturated, branched or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, such as, for example, jojoba oil.

In the case of a content of at least one pigment, at least one dye or at least one powder substance, the constituents of the fatty phase can also advantageously be chosen from the group of Guerbet alcohols. Guerbet alcohols are named after Marcel Guerbet, who describes their preparation for the first time. They are formed in accordance with the reaction equation

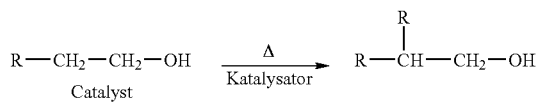

by oxidation of an alcohol to an aldehyde, by aldol condensation of the aldehyde, elimination of the water from the aldol and hydrogenation of the allyl aldehyde. Guerbet alcohols are themselves liquid at low temperatures and bring about virtually no skin irritations. They can be used advantageously as fatting, superfatting and also refatting constituents in skincare and hair care compositions.

The use of Guerbet alcohols in cosmetics is known per se. Such species are then characterized in most cases by the structure

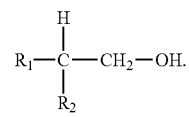

Here, $R_1$ and $R_2$ are generally unbranched alkyl radicals.

According to the invention, the Guerbet alcohol or Guerbet alcohols are chosen from the group in which $R_1$=propyl, butyl, pentyl, hexyl, heptyl or octyl and
$R_2$=hexyl, heptyl, octyl, nonyl, decyl, undecyl, dodecyl, tridecyl or tetradecyl.

Guerbet alcohols preferred according to the invention are 2-butyloctanol—it has the chemical structure

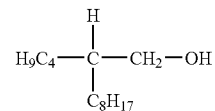

and is available, for example, under the trade name Isofol® 12 from Condea Chemie GmbH—and 2-hexyldecanol—it has the chemical structure

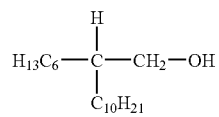

and is available, for example, under the trade name Isofol® 16 from Condea Chemie GmbH.

Mixtures of Guerbet alcohols according to the invention can also be used advantageously according to the invention. Mixtures of 2-butyloctanol and 2-hexyldecanol are available, for example, under the trade name Isofol® 14 from Condea Chemie GmbH.

The total amount of Guerbet alcohols in the finished stick formulation is advantageously chosen from the range up to 25.0% by weight, preferably 0.5-15.0% by weight, based on the total weight of the stick.

Nonpolar oils are, for example, those which are chosen from the group of branched and unbranched hydrocarbons and hydrocarbon waxes, in particular Vaseline (Petrolatum), paraffin oil, squalane and squalene, polyolefins and hydrogenated polyisobutenes. Among the polyolefins, polydecenes are the preferred substances. Table 1 below lists lipids which are advantageous according to the invention as individual substances or else in a mixture with one another. The corresponding interfacial tensions toward water are given in the last column. It is, however, also advantageous to use mixtures of higher and lower polarity and the like.

TABLE 1

1.1 Lipids advantageous according to the invention

| Trade name | INCI name | (mN/m) |
| --- | --- | --- |
| Isofol ® 14 T | Butyl Decanol + Hexyl Decanol + Hexyl Octanol + Butyl Octanol | 27.6 |
| Isofol ® 16 | Hexyl Decanol | 24.3 |
| Eutanol ® G | Octyldodecanol | 24.8 |
| Cetiol ® OE | Dicaprylyl Ether | 22.1 |
| Miglyol ® 812 | Caprylic/Capric Triglyceride | 21.3 |
| Cegesoft ® C24 | Octyl Palmitate | 23.1 |
| Isopropyl stearate | Isopropyl Stearate | 21.9 |
| Estol ® 1540 EHC | Octyl Octanoate | 30.0 |
| Finsolv ® TN | $C_{12-15}$ Alkyl Benzoate | 21.8 |
| Cetiol ® SN | Cetearyl Isononanoate | 28.6 |
| Dermofeel ® BGC | Butylene Glycol Caprylate/Caprate | 21.5 |
| Trivent ® OCG | Tricaprylin | 20.2 |
| MOD | Octyldodecyl Myristate | 22.1 |
| Cosmacol ® ETI | Di-$C_{12-13}$ Alkyl Tartrate | 29.4 |
| Miglyol ® 829 | Caprylic/Capric Diglyceryl Succinate | 29.5 |
| Prisorine ® 2036 | Octyl Isostearate | 29.7 |
| Tegosoft ® SH | Stearyl Heptanoate | 28.7 |
| Abil ® Wax 9840 | Cetyl Dimethicone | 25.1 |
| Cetiol ® LC | Coco-Caprylate/Caprate | 24.8 |
| IPP | Isopropyl Palmitate | 22.5 |
| Luvitol ® EHO | Cetearyl Octanoate | 28.6 |
| Cetiol ® 868 | Octyl Stearate | 28.4 |

In the case of a content of at least one pigment, at least one dye or at least one powder substance, the fatty phase is advantageously chosen from the group consisting of 2-ethylhexyl isostearate, octyidodecanol, isotridecyl isononanoate, isoeicosan, 2-ethylhexyl cocoate, $C_{12-15}$-alkyl benzoate, caprylic/capric triglyceride and dicaprylyl ether.

In the case of a content of at least one pigment, at least one dye or at least one powder substance, mixtures of octyldodecanol, caprylic/capric triglyceride and dicaprylyl ether, mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate are particularly advantageous.

In the case of a content of at least one pigment, at least one dye or at least one powder substance, of the hydrocarbons, paraffin oil, cycloparaffin, squalane, squalene, hydrogenated polyisobutene and polydecene are to be used advantageously for the purposes of the present invention.

The oil components can advantageously be present in a content of from 0.5 to 80% by weight, based on the total preparation, preference being given to about 1 to 20% by weight.

Waxes which can be used are unbranched, saturated or unsaturated, aliphatic fatty alcohols or fatty acids which have a chain length of from C22 to C60, it being possible for said alcohols and fatty acids to be present either individually or else in a mixture. Behenic acids and even longer-chain fatty acids (C24-60 fatty acids) are to be used particularly advantageously. In addition, these may also be branched. In the case of a content of at least one pigment, at least one dye or at least one powder substance, fatty or wax components may also be chosen from the group of plant waxes, animal waxes, mineral waxes and petrochemical waxes, it being preferred when the wax component or the totality of the wax components is chosen from the group of esters of saturated or unsaturated, branched or unbranched alkanecarboxylic acids with a chain length of from 1 to 80 carbon atoms and saturated or unsaturated, branched or unbranched alcohols with a chain length of from 1 to 80 carbon atoms, from the group of esters of aromatic carboxylic acids and saturated or unsaturated, branched or unbranched alcohols with a chain length of from 1 to 80 carbon atoms, provided the wax component or the totality of the wax components are a solid at room temperature. It is particularly preferred when the wax component or the totality of the wax components is chosen from the group of esters of saturated branched alkanecarboxylic acids with a chain length of from 14 to 44 carbon atoms and saturated branched alcohols with a chain length of from 14 to 44 carbon atoms, provided the wax component or the totality of the wax components are a solid at room temperature, natural waxes, diesters of polyols or C10-C80 fatty acids, ethoxylated waxes, triglyceride waxes, and C16-C60 fatty acids (or salts thereof) and C16-C80 fatty alcohols, where, according to the invention, candelilla wax, carnauba wax, Japan wax, espartograss wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes and microwaxes for example are favorable, provided the conditions required in the main claim are observed. Further advantageous fatty or wax components are chemically modified waxes and synthetic waxes, such as, for example, those available under the trade names Syncrowax HRC (glyceryl tribehenate), Syncrowax HGLC ($C_{16-36}$-fatty acid triglyceride) and Syncrowax AW 1C ($C_{18-36}$-fatty acid) from CRODA GmbH, and montan ester waxes, sasol waxes, hydrogenated jojoba waxes, polyalkylene waxes, polyethylene glycol waxes, but also chemically modified fats, such as, for example, hydrogenated vegetable oils (for example hydrogenated castor oil or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate or glycol montanate. The wax component or the totality of the wax components of the W/O emulsion sticks according to the invention is preferably chosen from the group of esters of saturated or unsaturated, branched or unbranched alkanecarboxylic acids with a chain length of from 14 to 44 carbon atoms and saturated or unsaturated, branched or unbranched alcohols with a chain length of from 14 to 44 carbon atoms, from the group of esters of aromatic carboxylic acids or hydroxycarboxylic acids (e.g. 12-hydroxystearic acid) and saturated or unsaturated, branched or unbranched alcohols with a chain length of from 3 to 30 carbon atoms, provided the wax component or the totality of the wax components are a solid at room temperature. It is preferred to choose the wax components from the group of esters of saturated branched alkanecarboxylic acids with a chain length of from 14 to 44 carbon atoms and saturated unbranched alcohols with a chain length of from 14 to 44 carbon atoms, provided the wax component or the totality of the wax components are a solid at room temperature, and
esters of saturated unbranched alkanecarboxylic acids with a chain length of from 14 to 44 carbon atoms and saturated branched alcohols with a chain length of from 14 to 44 carbon atoms, provided the wax component or the totality of the wax components are a solid at room temperature; and polyethylene waxes (Performalene 400), and it is particularly preferred to choose the wax components from the group of esters of saturated branched alkanecarboxylic acids with a chain length of from 14 to 44 carbon atoms and saturated branched alcohols with a chain length of from 14 to 44 carbon atoms, provided the wax component or the totality of the wax components are a solid at room temperature. The wax components can particularly advantageously be chosen from the group of $C_{16-36}$-alkyl stearates, of $C_{10-40}$-alkyl stearates, $C_{20-40}$-alkyl isostearates, of $C_{20-40}$-dialkyl dimerates, of $C_{18-38}$-alkylhydroxystearoyl stearates, of $C_{20-40}$-alkyl erucates, and also $C_{30-50}$-alkyl beeswax, cetearyl behenate, and polyethylene wax (Performalene 400). The wax components can advantageously be present in a content of from 0.5 to 80% by weight, based on the total preparation, preference being given to about 1 to 20% by weight; in addition, the wax components may either be present individually or else as a mixture. Preference is given to choosing a wax fraction of from 5 to 20% by weight. Preference is given to choosing the waxes from the group of ester waxes, particular preference being given to the ester waxes of long-chain unbranched alkyl chains. In addition, it is advantageous when the alkyl chains are of differing chain length; any mixtures of oil and wax components can be used advantageously for the purposes of the present invention.

The long-chain fatty acids can also be used in the form of their salts (soaps of monovalent, divalent or trivalent cations, such as, for example, calcium behenate).

Advantageously for the purposes of the present invention are, in particular, fatty alcohols or fatty alcohol mixtures which are obtainable by saponification of waxes or wax mixtures. Being natural products, the waxes or wax mixtures used as starting materials may be of varying composition.

Advantageous fatty alcohols or fatty alcohol mixtures are obtainable, for example, from beeswax, china wax, bumblebee wax and other insect waxes.

Fatty alcohols or fatty alcohol mixtures which are obtainable from plant waxes are also advantageous for the purposes of the present invention. Cuticular waxes of lower or higher plants, algae, lichen, moss and fungi, such as, for example, candelilla wax, carnauba wax, Japan wax, espartograss wax, cork wax, rice wax, sugarcane wax, fruit waxes, e.g. apple wax, blossom waxes, leaf waxes of softwoods, coffee wax, flax wax, sesame wax, jojoba oil and the like.

In addition, rice waxes, fruit waxes such as apple wax, orange wax, lemon wax, grapefruit wax, bayberry wax and the like can also be used advantageously. In addition, these natural waxes can also be used on their own without synthetic waxes.

In addition, it is also possible to use waxes of diesters of C10-C80 fatty acids, where the alcohol component chosen is propylene glycol, ethylene glycol, polyethylene glycol, polypropylene glycol, polyglycerol. In addition, pentaerythritol triorthotetraesters of C10 to C80 fatty acids or else corresponding fatty acids of the sorbitan triesters and sucrose polyesters with 3-8 mol degree of substitution can also be used.

For example, the ethylene glycol ester of C18-36-fatty acids (Syncrowax ERL-C) or else ethylene glycol distearates and glycol distearate is suitable.

In addition, waxes can be chosen from the group of esters of saturated or unsaturated, branched or unbranched alkanecarboxylic acids with a chain length of from 1 to 80 carbon atoms and saturated or unsaturated, branched or unbranched alcohols with a chain length of from 1 to 80 carbon atoms, from the group of esters of aromatic carboxylic acids or hydroxycarboxylic acids (e.g. 12-hydroxystearic acid) and saturated or unsaturated, branched or unbranched alcohols with a chain length of from 1 to 80 carbon atoms provided the wax component or the totality of the wax components are a solid at room temperature.

It is preferred to choose the wax components from the group of esters of saturated branched alkanecarboxylic acids with a chain length of from 1 to 60 carbon atoms and saturated unbranched alcohols with a chain length of from 1 to 60 carbon atoms, provided the wax component or the totality of the wax components are a solid at room temperature, and esters of saturated unbranched alkanecarboxylic acids with a chain length of from 1 to 60 carbon atoms and saturated branched alcohols with a chain length of from 1 to 60 carbon atoms, provided the wax component or the totality of the wax components are a solid at room temperature.

The wax components can be chosen particularly advantageously from the group of $C_{16-36}$-alkyl stearates, $C_{10-40}$-alkyl stearates, $C_{20-40}$-alkyl isostearates, $C_{20-40}$-dialkyl dimerates, $C_{18-38}$-alkylhydroxystearoyl stearates, $C_{20-40}$-dialkyl dimerates and $C_{20-40}$-alkyl erucates, and also $C_{30-50}$-alkyl beeswax, cetyl palmitate, methyl palmitate, cetearyl behenate and octacosanyl stearate. Silicone waxes, such as, for example, stearyltrimethylsilane/stearyl alcohol are also advantageous in some cases.

Also advantageous for the purposes of the present invention are ester waxes, which represent esters of 1. saturated or unsaturated, branched or unbranched mono- or dicarboxylic acid having 10 to 15 carbon atoms, preferably 15-45 carbon atoms and
2. glycerol.

In this connection, mono-, di- and triglycerides may be advantageous.

The glycerides listed below are particularly advantageous:

| Glyceride | Trade name | Available from |
| --- | --- | --- |
| $C_{16-18}$-Triglyceride | Cremeol HF-52-SPC | Aarhus Oliefabrik |
| Glyceryl hydroxystearate | Naturchem GMHS | Rahn |
| Hydrogenated cocoglycerides | Softisan 100 | Hüls AG |
| Caprylic/capric/isostearic adipic triglyceride | Softisan 649 | Dynamit Nobel |
| $C_{18-36}$Triglyceride | Syncrowax HGLC | Croda GmbH |
| Glyceryl tribehenate | Syncrowax HRC | Croda GmbH |
| Glyceryl tri(12-hydroxystearate) | Thixcin R | Rheox/NRC |
| Hydrogenated castor oil | Cutina HR | Henkel KGaA |
| $C_{16-24}$-Triglyceride | Cremeol HF-62-SPC | Aarhus Oliefabrik |

It is particularly preferred to choose the wax components from the group of triglyceride waxes such as C18-38 triglyceride or tribehenin.

In addition, it has been found that ethoxylated waxes, such as, for example, PEG-8 beeswax, PEG 6 sorbitan beeswax, PEG-2 hydrogenated castor oil, PEG-12 carnauba wax are advantageous since they make the stick matrix softer and also permit better solubilization of water-soluble ingredients.

In addition, it has been found that, besides the use of one of the above-described waxes, certain wax combinations are advantageous.

The wax components can advantageously be present in a content of from 0.5 to 80% by weight, based on the total preparation, preference being given to about 1 to 20% by weight.

It is advantageous to set the ratio of oil and wax components to one another approximately from the range of weight ratios between 4:1 to 1:4, in particular 3:1 to 1:3, very particularly preferably 2:1 to 1:2.

The amount of water can be up to about 85% by weight, based on the total weight of the preparations, with optimum water contents in the range between 30 and 80% by weight, preferably between 35 and 75% by weight, particularly preferably 50 and 75% by weight, very particularly preferably 45 to 65% by weight usually being chosen. If desired, the minimum water content can drop below 10% by weight. However, it is of greater advantage to equip emulsion sticks according to the invention with a content of more than 10% by weight of water, particularly when water-soluble or water-dispersible active ingredients, such as skin-moisturizing agents, antiacne agents, UV filters, concealing pigments, and water-dispersible pigments are to be used in concentrations known to the person skilled in the art.

Skin-moisturizing agents which may be used advantageously are glycerol, chitosan, Fucogel, propylene glycol, dipropylene glycol, butylene glycol, mannitol, lactic acid, sodium pyrrolidonecarboxylic acid, hyaluronic acid, salts of the acids given, and also glycine, urea and salts of metals of the first and second main group.

Glycerol, lactic acid, butylene glycol, urea, hyaluronic acid are particularly suitable, with glycerol being very particularly preferred.

The content of skin-moisturizing agents is advantageously 3% by weight to 60% by weight, preferably 4 to 50% by weight, in particular 5 to 40% by weight, based on the total weight of the preparations.

The water-rich sticks according to the invention are excellent vehicles for dermatological active ingredients. In particular, they are suitable as carriers for antiacne substances. For example, it is advantageous to add to the preparations used according to the invention substances which are effective against acne, for example substances which are effective against *Propionibacterium acnes* (for example those described in DE-A 42 29 707, DE-A 43 05 069, DE-A 43 07 976, DE-A 43 37 711, DE-A 43 29 379) but also other antiacne substances, for example all-trans retinoic acid, 13-cis-retinoic acid and related substances) or antiinflammatory active ingredients, for example batyl alcohol α-octadecyl glyceryl ether), selachyl alcohol (α-9-octadecenyl glyceryl ether), chimyl alcohol (α-hexadecyl glyceryl ether), bisabolol, acidic aluminum or zirconium salts, glyceryl caprate, 2-butyloctanoic acid, lactic acid, salicylic acid, zinc salts, citric acid, diglyceryl monocaprinate, glyceryl caprylate, polyglyceryl-3 caprylate and octoxy glycerol.

Of these, particularly preferred antiacne active ingredients are acidic aluminum or zirconium salts, lactic acid, salicylic acid, zinc salts, citric acid, diglycerol monocaprinate, glyceryl caprinate, 2-butyloctanoic acid, glyceryl caprylate, polyglyceryl-3 caprylate and octoxy glycerol. In particular, combinations of said active ingredients are also advantageous.

The amount of antiacne agents (one or more compounds) in the preparations is preferably 0.01 to 30% by weight, particularly preferably 0.1-20% by weight, in particular 1-10% by weight, based on the total weight of the preparation.

In addition, the process according to the invention is characterized in that a large number of emulsifiers or oil components can be used for the preparation of the sticks according to the invention.

W/O emulsifiers according to the invention are specified above.

It may be advantageous according to the invention that also other polyethoxylated and/or polypropoxylated emulsifiers are used, for example polyethoxylated hydrogenated or non-hydrogenated castor oil, ethoxylated cholesterol, ethoxylated fatty alcohols, such as steareth-2, ethoxylated fatty acids, ethoxylated dicarboxylic acids, ethoxylated waxes such as PEG (-6, -8, -12, -20) beeswax, PEG (-6, -8, -20 sorbitan beeswax), ethoxylated carnauba waxes (PEG-12 carnauba wax).

Particularly advantageous W/O emulsifiers are glyceryl lanolate, glyceryl monostearate, glyceryl monoisostearate, glyceryl monomyristate, glyceryl monooleate, diglyceryl monostearate, diglyceryl monoisostearate, diglyceryl diisostearate, propylene glycol monostearate, propylene glycol monoisostearate, propylene glycol diisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, 2-ethylhexyl glycerol ether, selachyl alcohol, chimyl alcohol, polyethylene glycol (2) stearyl ether (steareth-2), glyceryl monolaurate, glyceryl monocaprinate, glyceryl monocaprylate, glyceryl sorbitan stearate, polyglyceryl-4 isostearate, polyglyceryl-2 sesquiisostearate, PEG-7 hydrogenated castor oil, PEG-40 sorbitan perisostearate, isostearyl diglyceryl succinate, PEG-5 cholesteryl ether, and triglycerol diisostearate.

The W/O emulsifier used according to the invention or the W/O emulsifiers used according to the invention, which fits or fit into the scheme A-B-A', is or are advantageously present in concentrations of 0.1-25% by weight, although it is possible and advantageous to keep the content of emulsifiers low, for example up to 5% by weight, in each case based on the total weight of the composition. It is advantageous to choose the total concentration of the W/O emulsifiers, which also includes those emulsifiers which do not fit into the scheme A-B-A', to be not greater than about 25-30% by weight and not less than about 0.1% by weight, in each case based on the total weight of the preparations.

It may be advantageous according to the invention that the above-mentioned types of W/O emulsifiers are additionally polyethoxylated and/or polypropoxylated, or that also other polyethoxylated and/or polypropoxylated products are used, for example polyethoxylated hydrogenated or nonhydrogenated castor oil, ethoxylated cholesterol, and ethoxylated fatty alcohols, such as steareth-2.

The stabilizers according to the invention are advantageously chosen according to the invention from the group of substances of the general formula

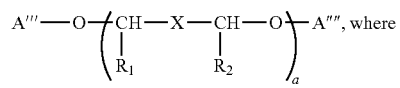

A''' and A'''' are identical or different hydrophobic organic radicals,
a is a number from 1 to 100, preferably 2 to 60, X is a single bond or the group

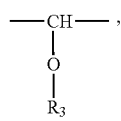

R$_1$ and R$_2$, independently of one another, are chosen from the group consisting of H, methyl, but such that both radicals are not methyl at the same time, and R$_3$ is chosen from the group consisting of H, and branched and unbranched, saturated and unsaturated alkyl and acyl radicals having 1-20 carbon atoms.

The structural formula should not be interpreted as meaning that, by virtue of the index a, all of the radicals R$_1$, R$_2$ and R$_3$ represented in the brackets have to be identical in each case within the entire molecule. Rather, these radicals may be chosen freely in each of the a fragments

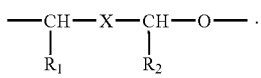

The radicals A''' and A'''' may be identical or different and are preferably chosen from the group

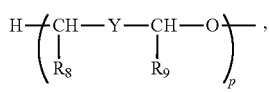

where R$_8$ and R$_9$ may be identical or different and are chosen from the group of saturated and unsaturated alkyl and acyl radicals having 1-30 carbon atoms, p is a number from 1-20 and Y is a single bond or the group

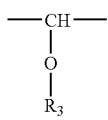

where R$_3$ is chosen from the group consisting of H, and branched and unbranched, saturated and unsaturated alkyl and acyl radicals having 1-30 carbon atoms.

A preferred stabilizer is the PEG-45/dodecyl glycol copolymer, which has the structure

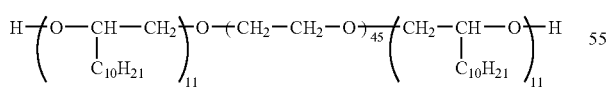

It is supplied by Akzo Nobel Chemicals GmbH under the name ELFACOS® ST 9. However, the corresponding PEG-22/dodecyl glycol copolymer can also be used advantageously.

In addition, the group A''' and A'''' may, independently of one another, also represent alkyl radicals or acyl radicals. It is also particularly advantageous to use the methoxy-PEG-22 dodecyl glycol copolymer as stabilizer. It is supplied by Akzo Nobel Chemicals GmbH under the name ELFACOS® E 200.

The stabilizer or the stabilizers are advantageously present in concentrations of 0.01-25% by weight, although it is possible and advantageous to keep the content of stabilizers low, for example up to 5% by weight, in each case based on the total weight of the composition.

In particular, it is then advantageous to choose stabilizers when preparations according to the invention are to comprise a high content of destabilizing substances, for example photoprotective filters. If the content of destabilizing substances is low, it is possible to dispense with the stabilizer.

In the case of a content of at least one pigment, at least one dye or at least one powder substance, the emulsions or sticks according to the invention can advantageously comprise one or more emulsifiers which are advantageously chosen from the group of the following surface-active substances of the type A-B-A'.

In this connection, it is preferred when the W/O emulsifier or the W/O emulsifiers are chosen from the group of substances of the general formula

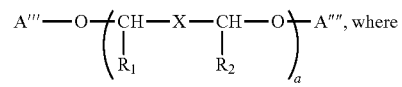

A''' and A'''' are identical or different hydrophobic organic radicals, a is a number from 1 to 100, preferably 2 to 60, X is a single bond or the group

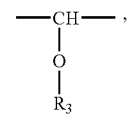

R$_1$ and R$_2$, independently of one another, are chosen from the group consisting of H, methyl, but such that both radicals are not methyl at the same time, and R$_3$ is chosen from the group consisting of H, and branched and unbranched, saturated and unsaturated alkyl and acyl radicals having 1-20 carbon atoms, where the radicals A''' and A'''' may be identical or different and are chosen from the group

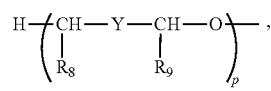

where R$_8$ and R$_9$ may be identical or different and are chosen from the group of saturated and unsaturated alkyl and acyl radicals having 1-30 carbon atoms, p is a number from 1-20 and Y is a single bond or the group

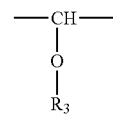

where R$_3$ is chosen from the group consisting of H, and branched and unbranched, saturated and unsaturated alkyl and acyl radicals having 1-30 carbon atoms.

In addition, in the case of a content of at least one pigment, at least one dye or at least one powder substance, the group A''' and A'''' may, independently of one another, also be alkyl radicals or acyl radicals.

In this connection, the stabilizer used is preferably the PEG-45/dodecyl glycol copolymer, the PEG-22/dodecyl glycol copolymer, PEG-30 dipolyhydroxystearates or the methoxy PEG-22/dodecyl glycol copolymer.

It is also advantageous in this connection when coemulsifiers are additionally present which are chosen from the group of substances of the general formula

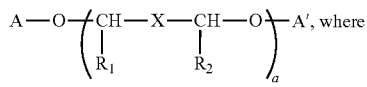

A and A' are identical or different hydrophobic organic radicals,

A is a number from 1 to 100, preferably 2 to 60, in particular 5 to 40,

X is a single bond or the group

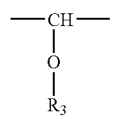

$R_1$ and $R_2$, independently of one another, are H, methyl, but chosen such that those radicals are not methyl at the same time, and $R_3$ is chosen from the group consisting of H, and also branched and unbranched, saturated and unsaturated alkyl and acyl radicals having 1-20 carbon atoms, or that the W/O coemulsifier(s) are chosen from the group of fatty alcohols having 8-30 carbon atoms, monoglycerol esters of saturated or unsaturated, branched or unbranched alkanecarboxylic acids with a chain length of 8-24, in particular 12-18, carbon atoms, diglycerol esters of saturated or unsaturated, branched or unbranched alkanecarboxylic acids with a chain length of 8-24, in particular 12-18, carbon atoms, triglycerol esters of saturated or unsaturated, branched or unbranched alkanecarboxylic acids with a chain length of 8-24, in particular 12-18, carbon atoms, polyglycerol esters of saturated or unsaturated, branched or unbranched alkanecarboxylic acids with a chain length of 8-24, in particular 12-18, carbon atoms with up to 10 glycerol units, monoglycerol ethers of saturated or unsaturated, branched or unbranched alcohols with a chain length of 8-24, in particular 12-18, carbon atoms, diglycerol ethers of saturated or unsaturated, branched or unbranched alcohols with a chain length of 8-24, in particular 12-18, carbon atoms, triglycerol ethers of saturated or unsaturated, branched or unbranched alcohols with a chain length of 8-24, in particular 12-18, carbon atoms, polyglycerol ethers of saturated or unsaturated, branched or unbranched alkanecarboxylic acids with a chain length of 8-24, in particular 12-18, carbon atoms, with up to 10 glycerol units, propylene glycol esters of saturated or unsaturated, branched or unbranched alkanecarboxylic acids with a chain length of 8-24, in particular 12-18, carbon atoms, sorbitan esters of saturated or unsaturated, branched or unbranched alkanecarboxylic acids with a chain length of 8-24, in particular 12-18, carbon atoms, sorbitan esters of polyols, in particular of glycerol, pentaerythrityl esters of saturated or unsaturated, branched or unbranched alkanecarboxylic acids with a chain length of 8-24, in particular 12-18, carbon atoms, methylglucose esters of saturated or unsaturated, branched or unbranched alkanecarboxylic acids with a chain length of 8-24, in particular 12-18, carbon atoms, polyglycerol methylglucose esters of saturated or unsaturated, branched or unbranched alkanecarboxylic acids with a chain length of 8-24, in particular 12-18, carbon atoms, or that the abovementioned types of W/O emulsifiers are additionally polyethoxylated and/or polypropoxylated in such a way that they are ethoxylated and/or propoxylated W/O emulsifiers.

In the case of a content of at least one pigment, at least one dye or at least one powder substance, it is particularly preferred when the W/O coemulsifier or the W/O coemulsifiers are chosen such that the radicals A and A' are advantageously chosen from the group of branched and unbranched, saturated and unsaturated alkyl and acyl radicals and hydroxyacyl radicals having 10-30 carbon atoms, and also from the group of hydroxyacyl groups joined together via ester functions, in accordance with the scheme

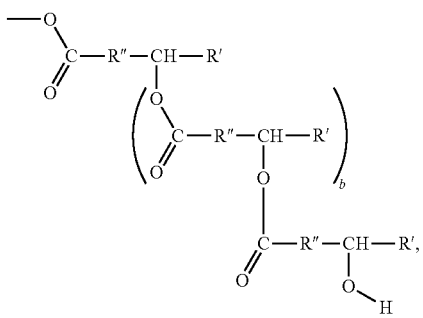

where R' is chosen from the group of branched and unbranched alkyl groups having 1 to 20 carbon atoms, R" is chosen from the group of branched and unbranched alkylene groups having 1 to 20 carbon atoms and b can assume numbers from 0 to 200.

In the case of a content of at least one pigment, at least one dye or at least one powder substance, it is very particularly preferred when the coemulsifier(s) are chosen from the group consisting of decaglyceryl heptaoleate, polyglyceryl-3 diisostearate, PEG-8 distearate, and diglycerol dipolyhydroxystearate; the use of an emulsifier/coemulsifier mixture in the range from 1 to 8% by weight has proven particularly suitable, particular preference being given to the use concentration at 2-6%. Here, the ratios of emulsifier to coemulsifier are preferably chosen to be from 1:0 to 1:1.

Furthermore, the emulsions according to the invention can comprise dyes or pigments. The dyes and color pigments can be chosen from the corresponding positive lists of the Cosmetics Directive or the EC list of cosmetic colorants. In most cases, they are identical to the dyes approved for foodstuffs. The pigments which can be used may be organic and inorganic in origin, such as, for example, organic ones of the azo type, indigoids, triphenylmethane-like ones, anthraquinones, and xanthine dyes, which are known as D&C and FD&C blues, browns, greens, oranges, reds and yellows. Inorganic ones consist of insoluble salts of certified dyes, which are referred to as lakes or iron oxides.

Colored pigments include inorganic and organic ones: barium lakes, calcium lakes, aluminum lakes, titanium dioxide, mica and iron oxides. Al salts which may be used are, for example, Red 3 aluminum lake, Red 21 aluminum lake, Red 27 aluminum lake, Red 28 aluminum lake, Red 33 aluminum lake, Yellow 5 aluminum lake, Yellow 6 aluminum lake, Yellow 10 aluminum lake, Orange 5 aluminum lake, Blue 1 aluminum lake and combinations thereof.

Iron oxides or oxide hydrates which are known and in some instances advantageous are, for example, cosmetic yellow oxide C22-8073 (Sunchemical) cosmetic oxide MC 33-120 (Sunchemical), cosmetic brown oxide C33-115 (Nordmann & Rassmann), cosmetic russet oxide C33-8075 (Sunchemical). An aluminosilicate which may be used is ultramarine blue (Les colorants Wacker).

Pearlescent pigments can also be incorporated into the emulsions according to the invention. These include natural pearlescent pigments, such as, for example, "pearl essence" (guanine/hypoxanthine mixed crystals from fish scales) and
"mother of pearl" (ground mussel shells),
monocrystalline pearlescent pigments, such as, for example, bismuth oxychloride (BiOCl), and
layer-substrate pigments: e.g. mica/metal oxide Bases for pearlescent pigments are, for example, pulverulent pigments or castor oil dispersions of bismuth oxychloride or titanium dioxide, and bismuth oxychloride or titanium dioxide on mica. The luster pigment listed under CIN 77163, for example, is particularly advantageous.

These are known, for example, from Costenoblé (cloisonne type, flamenco type, low luster type), Merck (colorona types, microna type, timiron type, colorona, Ronasphere), Les Colornats Wacker (Covapure, Vert oxyde de Chrome), Cadre (colorona, Sicopearl), BASF (Sicopearl, Sicovit), and Rona (colorona). Particularly advantageous pearlescent pigments have, for example, proven to be Timiron Silk Gold and Colorona Red Gold.

Also advantageous are, for example, the following types of pearlescent pigment based on mica/metal oxide:

| 1.1.1.1.1 Group | 1.1.1.2 Coating/layer thickness | 1.1.1.3 Color |
| --- | --- | --- |
| Silver-white pearlescent pigments | $TiO_2$: 40-60 nm | Silver |
| Interference pigments | $TiO_2$: 60-80 nm | Yellow |
| | $TiO_2$: 80-100 nm | Red |
| | $TiO_2$: 100-140 nm | Blue |
| | $TiO_2$: 120-160 nm | Green |
| Color luster pigments | $Fe_2O_3$ | Bronze |
| | $Fe_2O_3$ | Copper |
| | $Fe_2O_3$ | Red |
| | $Fe_2O_3$ | Red-violet |
| | $Fe_2O_3$ | Red-green |
| | $Fe_2O_3$ | Black |
| Combination pigments | $TiO_2/Fe_2O_3$ | Gold shades |
| | $TiO_2/Cr_2O_3$ | Green |
| | $TiO_2$/Prussian blue | Deep blue |
| | $TiO_2$/Carmine | Red |

The list of specified pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("ronaspheres"), which are sold by Merck and are particularly suitable for the optical reduction of fine lines are advantageous.

It may, moreover, be advantageous to dispense completely with a substrate such as mica. Particular preference is given to pearlescent pigments which are prepared with the use of $SiO_2$. Such pigments, which may also additionally have gonichromatic effects, are available, for example, under the trade name Sicopearl Fantastico from BASF.

In addition, pigments from Engelhard/Mearl based on calcium sodium borosilicate coated with titanium dioxide may be used advantageously. These are available under the name Reflecks. In addition to the color, they have a glitter effect as a result of their particle size of from 40-180 μm.

The cosmetic and dermatological preparations according to the invention can comprise dyes or color pigments, particularly when they are in the form of decorative lipsticks, lipliner pencils, concealing sticks, kohl pencils, eyeliner pencils or eyebrow pencils. The dyes and color pigments may be chosen from the corresponding positive list of the Cosmetics Directive or the EC list of cosmetic colorants. In most cases, they are identical to the dyes approved for foodstuffs. Advantageous color pigments are, for example, titanium dioxide, mica, iron oxides (e.g. $Fe_2O_3$, $Fe_3O_4$, FeO(OH)) and tin oxide. Advantageous dyes are, for example, carmine, Prussian blue, chrome oxide green, ultramarine blue and manganese violet. It is particularly advantageous to choose the dyes or color pigments from the following list. (The substances are ordered according to their Color Index Number. The Color Index Numbers (CIN) are taken from the *Rowe Colour Index, 3rd Edition, Society of Dyers and Colourists*, Bradford, England, 1971).

| Chemical or other name | CIN | Color |
| --- | --- | --- |
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |

| Chemical or other name | CIN | Color |
|---|---|---|
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4'-[(4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotenaldehyde ($C_{30}$) | 40820 | orange |
| trans-Apo-8'-carotenoic ($C_{30}$)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenylcarbinol | 42051 | blue |
| 4-[(4-N-Ethyl-p-sulfobenzylamino)phenyl(4-hydroxy-2-sulfophenyl)(methylene)-1-(N-ethyl-N-p-sulfobenzyl-2,5-cyclohexadienimine] | 42053 | green |
| Acid Blue 7 | 42080 | blue |
| (N-Ethyl-p-sulfobenzylamino)phenyl(2-sulfophenyl)methylene-(N-ethyl-N-p-sulfobenzyl)$\Delta^{2,5}$-cyclohexadienimine | 42090 | blue |
| Acid Green 9 | 42100 | green |
| Diethyldisulfobenzyl-di-4-amino-2-chloro-di-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4''-(N-diethyl)amino-2-methyl-N-ethyl-N-m-sulfobenzylfuchsonimmonium | 42735 | blue |
| 4'-(N-Dimethyl)amino-4''-(N-phenyl)aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanins | 74260 | green |
| Natural Yellow 6, 19; Natural Red 1 | 75100 | yellow |
| Bixin, Norbixin | 75120 | orange |
| Lycopene | 75125 | yellow |
| trans-alpha-, beta- and gamma-carotene | 75130 | orange |
| Keto- and/or hydroxyl derivatives of carotene | 75135 | yellow |
| Guanine or pearlescent agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide Hydrate | 77492 | yellow |
| Iron oxide | 77499 | black |
| Mixtures of iron (II) and iron(III)hexacyanoferrate | 77510 | blue |
| Pigment White 18 | 77713 | white |
| Manganese animonium diphosphate | 77742 | violet |
| Manganese phosphate; $Mn_3(PO_4)_2 \cdot 7 H20$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar coloring | | brown |
| Capsanthin, capsorubin | | orange |
| Betanin | | red |
| Benzopyrylium salts, anthocyans | | red |
| Aluminum, zinc, magnesium and calcium stearate | | white |
| Bromothymol blue | | blue |
| Bromocresol green | | green |
| Acid Red 195 | | red |

The use of inorganic color pigments such as red and black iron oxide (CIN: 77 491 (red) and 77 499 (black)), iron oxide hydrate (CIN: 77 492), manganese ammonium diphosphate, ultramarine, chromium oxide and chromium hydroxide, iron hexacyanoferrate and titanium dioxide is particularly preferred.

In this connection, preparations according to the invention comprise a titanium dioxide, which may be present either in the crystal modification rutile or anatase and, for the purposes of the present invention, is advantageously surface-treated ("coated"), the intention being, for example, to form or retain a hydrophilic, amphiphilic or hydrophobic character. This surface treatment can consist in providing the pigments with a thin hydrophilic or hydrophobic inorganic or organic layer by processes known per se. The various surface coatings may also comprise water for the purposes of the present invention.

For the purposes of the present invention, inorganic surface coatings may consist of aluminum oxide ($Al_2O_3$), aluminum hydroxide $Al(OH)_3$, aluminum oxide hydrate (also: alumina, CAS No. 1333-84-2), sodium hexametaphosphate ($NaPO_3)_6$, sodium metaphosphate ($NaPO_3)_n$, silicon dioxide ($SiO_2$) (also: silica, CAS No. 7631-86-9), zirconium oxide ($ZrO_2$) or iron oxide ($Fe_2O_3$). These inorganic surface coatings may be found on their own, in combination or in combination with organic coating materials.

For this purpose, oxides, oxide hydrates or phosphates of, for example, the elements Al, Si, Zr are deposited in thick layers onto the pigment surface. The inorganic after-treatment generally takes place in an aqueous suspension of the pigment through addition of soluble after-treatment chemicals, such as, for example, aluminum sulfate, and subsequent precipitation of the hydroxide sparingly soluble in the neutral range by targeted adjustment of the pH using sodium hydroxide solution. After the inorganic after-treatment, the coated pigments are separated from the suspension by filtration and carefully washed in order to remove the dissolved salts, then the isolated pigments are dried.

For the purposes of this invention, particular preference is given to titanium dioxide, onto which aluminum hydroxide has been applied on the surface, such as, for example, the titanium dioxide grades C47-051 and C4-5157 obtainable from Sun Chemical. Further preferred pigments are titanium dioxides which have been coated with aluminum oxides and/or silicon oxides, such as, for example, from Krosnos Titan: Kronos 1071 and 1075 or from Kingfisher: A310.03 Tudor Aspen.

Organic surface coatings for the purposes of the present invention can consist of vegetable or animal aluminum stearate, vegetable or animal stearic acid, lauric acid, dimethylpolysiloxane (also: dimethicone), methylpolysiloxane (methicones), simethicone (a mixture of dimethylpolysiloxane with an average chain length of from 200 to 350 dimethylsiloxane units and silica gel) or alginic acid. These organic surface coatings may be found on their own, in combination or in combination with inorganic coating materials.

The dyes and pigments may either be present individually or in a mixture, and be mutually coated with one another, various coating thicknesses generally giving rise to different color effects. The total amount of the dyes and color-imparting pigments is advantageously chosen from the range from, for example, 0.1% by weight to 30% by weight, preferably from 0.5 to 15% by weight, in particular from 1.0 to 10% by weight, in each case based on the total weight of the preparations.

The list of specified dyes and color pigments which can be used in the emulsion sticks according to the invention is not of course intended to be limiting.

Fillers for the purposes of the present invention are particulate substances which do not usually produce a color effect in the cosmetic formulation in which they are used. In addition, fillers according to the invention usually have a low refractive index and consequently no or only very slight coverage.

The prior art knows a series of fillers which are used, for example, as carrier materials in the formulation of powders or as viscosity and sensory modulators in emulsions or anhydrous formulations. Fillers of this type are also often used in order to attain matting effects on the skin, or to absorb sebum.

Moreover, the use of fillers generally also influences the distributability of customary formulations on the skin, and also the uniformity of a possible color effect.

The fillers for the purposes of the present invention are advantageously chosen from the group of inorganic fillers, for example from the group of silicates.

Silicates are salts and esters (silicic esters) of orthosilicic acid [$Si(OH)_4$] and condensation products thereof. The silicates are not only the species-richest class of minerals, but are also extremely important in geological and technical terms. More than 80% of the earth's crust consists of silicates.

For the purposes of the present invention, sheet silicates, for example, are advantageous. Sheet silicates (phyllosilicates, layer silicates) are (ideally) silicate structures with two-dimensionally infinite layers of $[SiO_4]^{-4}$ tetrahedra, where each tetrahedron is bonded to adjacent tetrahedra via 3 bridging oxygens.

Chemical formulae for sheet silicates can only be drawn up in approximate terms since they have a large ion-exchange capacity, and silicon can be exchanged for aluminum, which in turn can be exchanged for magnesium, $Fe^{2+}$, $Fe^{3+}$, Zn and the like. The negative charge of the layers which possibly results from this is usually balanced by cations, in particular by $Na^+$ and $Ca^{2+}$ in interlayer positions.

Sheet silicates can swell as a result of reversible intercalation of water (in a 2- to 7-fold amount) and other substances, such as, for example, alcohols, glycols and the like. Their use as thickeners in cosmetic compositions is, accordingly, known per se. However, the prior art was unable to point the way to the present invention.

Advantageous sheet silicates which can be used for the purposes of the present invention are, for example, those whose greatest expansion direction in the unmodified and unswollen state has, on average, a length of less than 10 μm. For example, the average expansions of the modified sheet silicate particles used can be 1000 nm×100 nm×1 nm and below. The effective size of the modified sheet silicate particles in a cosmetic or dermatological formulation naturally depends on the amount of intercalated substances.

(Sheet) silicates advantageous according to the invention are, in particular:
⇒ talc: $Mg_3[Si_4O_{10}](OH)_2$,
⇒ kaolin: $Al_2[Si_2O_5](OH)_4$
⇒ montmorillonite: $M^+Al[Si_2O_5](OH)$, also called smectites. These include:
bentonites=montmorillonites with Ca (fuller's earth) or Na (Wyoming bentonites)
hectorites: $M^+_{0.3}(Mg_{2.7}Li_{0.3})[Si_4O_{10}(OH)_2]$, in which $M^+$ is in most cases $Na^+$,
mica, an alumosilicate, which can be cleaved easily and is present in slab-like crystals. Mica is transparent to translucent and has pearlescence. The most important form is muscovite: $KAl_2[AlSi_3O_{10}](OH, F)_2$. Sericite is a particular form of mica which has smaller platelets than muscovite.

Silicon oxides (SiO$_2$) can also be used advantageously for the purposes of the present invention. According to the invention, preference is given, for example, to Aerosils (fumed silica), which are highly disperse silicas of often irregular shape whose specific surface area is generally very large (200-400 m$^2$/g) and can be controlled by means of the preparation process. Aerosils are also referred to as: amorphous silica, amorphous silicon oxide, hydrate silica, amorphous silicic anhydride and silicon dioxide.

Aerosils advantageous according to the invention are available, for example, under the following trade names: Aerosil 130 (Degussa Huls), Aerosil 200 (Degussa Huls), Aerosil 255 (Degussa Huls), Aerosil 300 (Degussa Huls), Aerosil 380 (Degussa Huls), B-6C (Suzuki Yushi), CAB-O-SIL Fumed Silica (Cabot), CAB-O-SIL EH-5 (Cabot), CAB-O-SIL HS-5 (Cabot), CAB-O-SIL LM-130 (Cabot), CAB-O-SIL MS-55 (Cabot), CAB-O-SIL M-5 (Cabot), E-6C (Suzuki Yushi), Fossil Flour MBK (MBK), MSS-500 (Kobo), Neosil CT 11 (Crosfield Co.), Ronasphere (Rona/EM Industries), Silica, Anhydrous 31 (Whittaker, Clark & Daniels), Silica, Crystalline 216 (Whittaker, Clark & Daniels), Silotrat-1 (Vevy), Sorbosil AC33 (Crosfield Co.), Sorbosil AC 35 (Crosfield Co.), Sorbosil AC 37 (Crosfield Co.), Sorbosil AC 39 (Crosfield Co.), Sorbosil AC77 (Crosfield Co.), Sorbosil TC 15 (Crosfield Co.), Spherica (Ikeda), Spheriglass (Potters-Ballotini), Spheron L-1500 (Presperse), Spheron N-2000 (Presperse), Spheron P-1500 (Presperse), Wacker HDK H 30 (Wacker-Chemie), Wacker HDK N 20 (Wacker-Chemie), Wacker HDK P 100H (Wacker Silicones), Wacker HDK N 20P (Wacker-Chemie), Wacker HDK N 25P (Wacker-Chemie), Wacker HDK S 13 (Wacker-Chemie), Wacker HDK T 30 (Wacker-Chemie), Wacker HDK V 15 (Wacker-Chemie), Wacker HDK V 15P (Wacker-Chemie), and Zelec Sil (DuPont).

Silicon oxides can also be prepared in spherical form, the specific surface area here being smaller than in the case of the Aerosils since the particles are larger and round. One example of this is the ronaspheres (average particle diameter <3µ) from Merck. Their use is preferred.

Further fillers preferred according to the invention are silicon dioxides whose free OH groups on the particle surface are (completely or partially) organically modified.

Of advantage are, for example, the silica dimethylsilylates obtainable by addition of dimethylsilyl groups, such as, for example, Aerosil R972 (Degussa Hüls), Aerosil R974 (Degussa Huls), CAB-O-SIL TS-610 (Cabot), CAB-O-SIL TS-720 (Cabot), Wacker HDK H15 (Wacker-Chemie), Wacker HDK H18 (Wacker-Chemie) and Wacker HDK H$_2$O (Wacker-Chemie).

Also advantageous are the silica silylates obtainable by addition of trimethylsilyl groups (e.g. Aerosil R 812 (Degussa Hüls), CAB-O-SIL TS-530 (Cabot), Sipernat D 17 (Degussa Hüls), and Wacker HDK H2000 (Wacker-Chemie)).

Also advantageous for the purposes of the present invention are the polymethylsilsesquioxanes obtainable by hydrolysis and condensation reactions of methyltrimethoxysilanes, which likewise have a round shape and whose particle size distribution can be controlled by the preparation.

Preferred polymethylsilsesquioxanes are supplied, for example, under the trade names Tospearl 2000 B from GE Bayer Silikones, Tospearl 145A from Toshiba, AEC Silicone Resin Spheres from A & E Connock and Wacker-Belsil PMS MK from Wacker-Chemie.

A further advantageous filler for the purposes of the present invention is boron nitride. Boron nitride is isoelectronic with carbon (i.e. graphite and diamond forms are possible). Boron nitride is characterized by its chemical inertness.

Advantageous for the purposes of the present invention are, for example, the boron nitrides listed below:

| Trade name | Available from: |
|---|---|
| Boron Nitride Powder | Advanced Ceramics |
| Boron Nitride Powder | Sintec Keramik |
| Ceram Blanche | Kawasaki |
| HCST Boron Nitride | Stark |
| Très BN ® | Carborundum |
| Wacker-Bornitrid BNP | Wacker-Chemie |

The fillers for the purposes of the present invention are moreover advantageously chosen from the group of organic fillers.

Organic fillers advantageous according to the invention are, for example, natural polymers, such as silk powders, microcrystalline cellulose and zinc stearates.

Advantageous organic fillers are also starch and starch derivatives, such as:
⇒ corn starch *Zea Mays* (Amidon De Mais MST (Wackherr), Argo Brand Corn Starch (Corn Products), Pure-Dent (Grain Processing), Purity 21C (National Starch)),
⇒ rice starch (D.S.A. 7 (Agrana starch), Oryzapearl (Ichimaru Pharcos)),
⇒ distarch phosphate (Corn PO$_4$ (Agrana starch), Corn PO$_4$ (Tri-K)),
⇒ sodium corn starch octenylsuccinate (C* EmCap—Instant 12639 (Cerestar USA)), and
⇒ aluminum starch octenylsuccinate (Covafluid AMD (Wackherr), Dry Flo-PC (National Starch), Dry Flo Pure (National Starch), Fluidamid DF 12 (Roquette)).

Organic fillers preferred according to the invention are also synthetic polymers, i.e. polymer particles which are present in the preparation in the form of solids, such as, for example, polycarbonates, polyethers, polyethylene, polypropylene, polyvinyl chloride, polystyrene, polyamides, polyurethanes, polyacrylates and the like. The substance of the INCI name HDI/Trimethylol Hexyllactone Crosspolymer, which is available under the name BPD-500/Plastic Powder D from Kobo is particularly advantageous for example.

Also advantageous for the purposes of the present invention is nylon (polyamide 6 and polyamide 12), such as, for example, microfine polyamide particles, in particular those available under the trade name SP-500 from TORAY. Also advantageous are polyamide 6 (also: nylon 6) or polyamide 12 (also: nylon 12) particles. Polyamide 6 is the polyamide [poly(ε-caprolactam)] built from ε-aminocaproic acid (ε-aminohexanoic acid), or ε-caprolactam, and polyamide 12 is a poly(ε-laurolactam) from ε-laurolactam. For the purposes of the present invention, Orgasol® 1002 (polyamide 6), and Orgasol® 2002 (polyamide 12) from ELF ATOCHEM, for example, are advantageous.

Further advantageous organic fillers are:
⇒ PMMA: polymethyl methacrylate,
⇒ polyethylene spheres,
⇒ polyurethanes,
⇒ silicone resins: trimethylsiloxysilicates (e.g. SR 1000 GE Bayer silicones),
⇒ silicone elastomers, and
⇒ polytetrafluoroethylene (PTFE).

Thus, it may be of considerable advantage, for example, to use in preparations according to the present invention those silicone elastomers that are described, for example, in U.S. Pat. No. 4,980,167 or U.S. Pat. No. 4,742,142. Advantageous silicone elastomers are also, for example, those which are sold under the names KSG6 from Shin Etsu, Trefil E-505C or Trefil E-506C from Dow Corning, Gransil from Grant Industries (SR-CYC, SR-DMF10, SR-DC556), and also those which are sold in the form of prepared gels (such as, for example, KSG15, KSG17, KSG16, KSG18 from Shin Etsu, Gransil SP 5CYC Gel, Gransil SR DMF 10 Gel, Gransil SR DC 556 Gel, Gransil GCM, Gransil PM Gel, Gransil DMG-5, SF 1204 and JK 113 from General Electric). Further advantageous silicone elastomers may be chosen from the group of vinyl dimethicone crosspolymers, such as, for example, the Dow Corning 9506 Cosmetic Powder from Dow Corning (INCI: Dimethicone/Vinyl Dimethicone Crosspolymer).

In addition, so-called silicone resins can be used advantageously, such as, for example, KSP-100, KSP-200 or KSP-300 from Shin Etsu, which are likewise recorded under the INCI name Dimethicone/Vinyl Dimethicone Crosspolymer, or SR 1000 from GE Bayer Silicones, which has the INCI name Trimethylsiloxy Silicate.

In addition, preference is also given to lauroyl lysine, which is sold under the name Amihope LL from Ajinomoto.

The total amount of at least one filler in the finished cosmetic or dermatological preparations is advantageously chosen from the range 0.05-20.0% by weight, preferably 0.5-10.0% by weight, based on the total weight of the preparations.

In addition, the preferred inorganic silicon compounds include the spherical particles organically modified on the surface. Of these, particular preference is given to the polymethylsilsesquioxanes and hydrophobically modified Aerosils, such as, for example, Aerosil R 972.

The preferred organic silicone compounds include the siloxane elastomers and siloxane resins. Of these, particular preference is given to the KSP grades from Shin Etsu, and trimethylsiloxysilicate.

Further fillers preferred according to the invention are from the group of spherical particles. Particularly preferably, the average particle diameter is less than 20 μm. Furthermore, preference is given to spherical particles with an average particle diameter of less than 10 μm. Of these, particular preference is given to nylon-12, which is sold, for example, as SP-501 or SP-500 by Kobo. Preference is also given to polymethyl methacrylates which are sold, for example, under the trade name Covabead LH 85 from LCW.

In addition, lauroyl lysine and bismuth oxychloride can preferably be used.

In addition, it is in accordance with the invention to add preservatives to the stick. Preservatives approved in food technology, which are listed below with their E numbers, are to be used advantageously according to the invention.

| E 200 | Sorbic acid |
| E 201 | Sodium sorbate |
| E 202 | Potassium sorbate |
| E 203 | Calcium sorbate |
| E 210 | Benzoic acid |
| E 211 | Sodium benzoate |
| E 212 | Potassium benzoate |
| E 213 | Calcium benzoate |
| E 214 | Ethyl p-hydroxybenzoate |
| E 215 | Ethyl p-hydroxybenzoate Na salt |
| E 216 | n-Propyl p-hydroxybenzoate |
| E 217 | n-Propyl p-hydroxybenzoate Na salt |
| E 218 | Methyl p-hydroxybenzoate |
| E 219 | Methyl p-hydroxybenzoate Na salt |
| E 220 | Sulfur dioxide |
| E 221 | Sodium sulfite |
| E 222 | Sodium hydrogensulfite |
| E 223 | Sodium disulfite |
| E 224 | Potassium disulfite |
| E 226 | Calcium sulfite |
| E 227 | Calcium hydrogensulfite |
| E 228 | Potassium hydrogensulfite |

-continued

| E 230 | Biphenyl (diphenyl) |
| E 231 | Orthophenylphenol |
| E 232 | Sodium orthophenylphenoxide |
| E 233 | Thiabendazole |
| E 235 | Natamycin |
| E 236 | Formic acid |
| E 237 | Sodium formate |
| E 238 | Calcium formate |
| E 239 | Hexamethylenetetramine |
| E 249 | Potassium nitrate |
| E 250 | Sodium nitrite |
| E 251 | Sodium nitrate |
| E 252 | Potassium nitrate |
| E 280 | Propionic acid |
| E 281 | Sodium propionate |
| E 282 | Calcium propionate |
| E 283 | Potassium propionate |
| E 290 | Carbon dioxide |

Also suitable according to the invention are preservatives or preservative auxiliaries customary in cosmetics dibromocyanobutane (2-bromo-2-bromomethylglutarodinitrile), 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride and benzyl alcohol.

These are preservatives or preservative auxiliaries customary in cosmetics, as are also listed in the Cosmetics Directive. Particular preference is given to using 3-iodo-2-propynyl butylcarbamate imidazolidinylurea, diazolinidylurea (e.g. available from ISP Sutton Laboratories under the trade name Germall II), 5-chloro-2-methyl-4-isothiazolin-3-one and 2-methyl-4-isothiazolone, which are sold as a mixture under the trade names Kathon CG and Rokonsal S1, 1,3-dimethyloyl-5,5-dimethylhydantoin, which is sold on its own under the name Glydant from Lonza, or in a mixture with 3-iodo-2-propynyl butylcarbamate under the name Glydant Plus, 2. Also suitable as preservatives are phenyl hydroxyalkyl ethers, in particular the compound known under the name phenoxyethanol due to its bactericidal and fungicidal effects on a number of microorganisms. Further preferred is also silver chloride, which is sold, for example, by Johnson Matthey as a mixture with titanium dioxide under the name JM Acticare.

Other germicidal agents are also likewise suitable to be incorporated into the preparations according to the invention. Advantageous substances are, for example, 2,4,4'-trichloro-2'-hydroxydiphenyl ether (Irgasan), 1,6-di(4-chlorophenyl-biguanido)-hexane (chlorhexidine), 3,4,4'-trichlorocarbanilide, quaternary ammonium compounds, oil of cloves, mint oil, oil of thyme, triethyl citrate, farnesol (3,7,11-trimethyl-2,6,10-dodecatrien-1-ole) and the active ingredients or active ingredient combinations described in the patent laid-open specifications DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004 and DE-196 34 019 and the patent specifications DE-42 29 737, DE-42 37 081, DE-43 24 219, DE-44 29 467, DE-44 23 410 and DE-195 16 705. Sodium hydrogencarbonate is also to be used advantageously.

Due to the high water phase content in the emulsions according to the invention, large amounts of hydrophilic active ingredients, and also hydrophobic active ingredients can be incorporated into the formulations. Such active ingredients advantageous according to the invention are, for example, acetylsalicylic acid, azulen, ascorbic acid, vitamin $B_1$, Vitamin $B_{12}$, vitamin $D_1$, but also bisabolol, unsaturated fatty acids, namely the essential fatty acids (often also called vitamin F), in particular γ-linolenic acid, oleic acid, eicosapentaneoic acid, docosahexaneoic acid, camphor, extracts or other products of vegetable and animal origin, e.g. evening primrose oil, borage oil or currant seed oil, fish oils, cod-liver oil and also ceramides and ceramide-like compounds and so on.

In addition, care active ingredients can be incorporated which are not limited as before to the fat-soluble active ingredients, but can also be chosen from the group of water-soluble active ingredients, for example vitamins and the like.

Particularly preferred active ingredients for the purposes of the present invention are α-glucosylrutin, coenzyme Q10, 3-hydroxy-4-(timethylammonio)butyrobetaine and sericoside.

Advantageous active ingredients are also antioxidants, in particular those which can protect not only the constituents of the formulation, but also the skin, against oxidative stress.

The preparations therefore advantageously comprise one or more antioxidants. Favorable, but nevertheless optional, antioxidants which may be used are all antioxidants customary or suitable for cosmetic or dermatological applications. It is advantageous to use antioxidants as the sole active ingredient class when, for example, a cosmetic or dermatological application is of prime importance, such as the combating of oxidative stress of the skin. It is, however, also favorable to provide the W/O emulsion sticks according to the invention with a content of one or more antioxidants if the preparations are to serve another purpose, e.g. as deodorants or sunscreen compositions.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioglycerol, thiosorbitol, thioglycolic acid, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), isoascorbic acid and its derivatives, tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these listed active ingredients which are suitable according to the invention.

For the purposes of the present invention, although oil-soluble or oil-dispersible antioxidants can be used particularly advantageously, it has been found that the invention opens the gates particularly to the use of water-soluble or water-dispersible antioxidants in stick formulations.

The amount of antioxidants (one or more compounds) in the preparations is preferably 0.001 to 30% by weight, particularly preferably 0.05 to 20% by weight, in particular 1 to 10% by weight, based on the total weight of the preparation.

If vitamin E or derivatives thereof are the antioxidant(s), it is advantageous to choose their respective concentrations from the range from 0.001 to 10% by weight, based on the total weight of the formulation.

If vitamin A or vitamin A derivatives, or carotenes or derivatives thereof are the antioxidant(s), it is advantageous to choose their respective concentrations from the range from 0.001 to 10% by weight, based on the total weight of the formulation.

According to the invention, active ingredients can also very advantageously be chosen from the group of lipophilic active ingredients, in particular from the following group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentaenoic acid, docosahexaenoic acid and derivatives thereof, chloroamphenicol, caffeine, prostaglandins, thymol, camphor, extracts or other products of vegetable and animal origin, e.g. evening primrose oil, borage oil or currant seed oil, fish oils, cod-liver oil and also ceramides and ceramide-like compounds and so on.

It is also advantageous to choose the active ingredients from the group of refatting substances, for example purcellin oil, Eucerit® and Neocerit®.

The sticks according to the invention additionally advantageously contribute to skin smoothing, particularly when they are provided with one or more substances which promote skin smoothing.

A surprising property of the preparations according to the invention is that they are very good vehicles for cosmetic or dermatological active ingredients into the skin, preferred active ingredients being antioxidants which can protect the skin against oxidative stress. Preferred antioxidants are vitamin E and derivatives thereof, and vitamin A and derivatives thereof.

The active ingredient(s) are also particularly advantageously chosen from the group of NO synthase inhibitors, particularly if the preparations according to the invention are to be used for the treatment and prophylaxis of the symptoms of intrinsic or extrinsic skin aging and for the treatment and prophylaxis of the harmful effects of ultraviolet radiation on the skin.

A preferred NO synthase inhibitor is nitroarginine.

The active ingredient(s) are also advantageously chosen from the group which includes catechins and bile esters of catechins and aqueous or organic extracts from plants or parts of plants which have a content of catechins or bile esters of catechins, such as, for example, the leaves of the *Theaceae* plant family, in particular of the species *Camellia sinensis* (green tea). Particularly advantageous are typical ingredients thereof (such as e.g. polyphenols or catechins, caffeine, vitamins, sugars, minerals, amino acids, and lipids).

Catechins are a group of compounds which are to be regarded as hydrogenated flavones or anthocyanidines and are derivatives of "catechin" (catechol, 3,3',4',5,7-flavanpentaol, 2-(3,4-dihydroxyphenyl)chroman-3,5,7-triol). Epicatechin ((2R,3R)-3,3',4',5,7-flavanpentaol) is also an advantageous active ingredient for the purposes of the present invention.

Also advantageous are plant extracts with a content of catechins, in particular extracts of green tea, such as e.g. extracts from leaves of plants of the species Camellia spec., very particularly the types of tea Camellia sinenis, C. assamica, C. taliensis and C. irrawadiensis and hybrids of these with, for example, Camellia japonica.

Preferred active ingredients are also polyphenols or catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin and (−)-epigallocatechin gallate.

Flavone and its derivatives (also often collectively called "flavones") are also advantageous active ingredients for the purposes of the present invention. They are characterized by the following basic structure (substitution positions are shown):

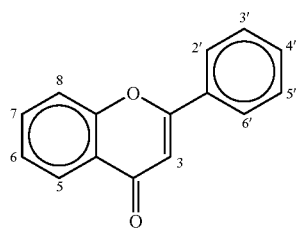

Some of the more important flavones which can also preferably be used in preparations according to the invention are given in the table below:

| | \multicolumn{8}{c|}{OH substitution positions} |
| --- | --- | --- | --- | --- | --- | --- | --- | --- |
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually in glycosylated form.

According to the invention, the flavonoids are preferably chosen chosen from the group of substances of the generic structural formula

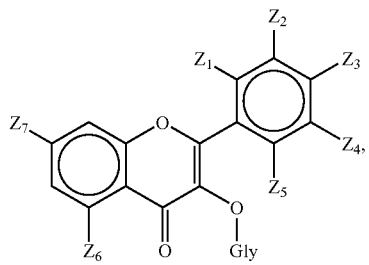

where $Z_1$ to $Z_7$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

According to the invention, the flavonoids can however, also advantageously be chosen from the group of substances of the generic structural formula

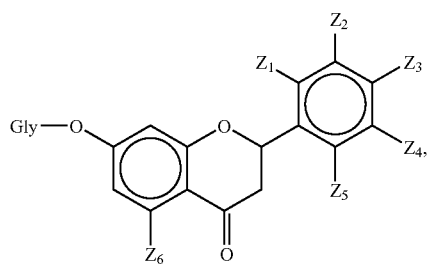

where $Z_1$ to $Z_6$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

Preferably, such structures can be chosen from the group of substances of the generic structural formula

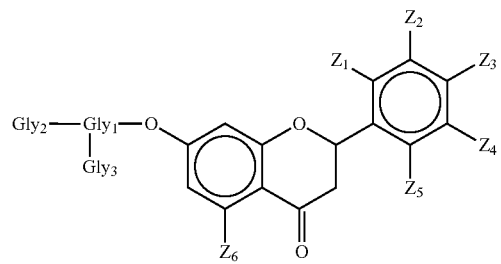

where $Gly_1$, $Gly_2$ and $Gly_3$, independently of one another, are monoglycoside radicals or. $Gly_2$ and $Gly_3$ can also, individually or together, represent saturations by hydrogen atoms.

Preferably, $Gly_1$, $Gly_2$ and $Gly_3$, independently of one another, are chosen from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, can also be used advantageously in some circumstances. It may also be advantageous according to the invention to use pentosyl radicals.

$Z_1$ to $Z_5$, independently of one another, are advantageously chosen from the group consisting of H, OH, methoxy, ethoxy and 2-hydroxyethoxy, and the flavone glycosides have the structure

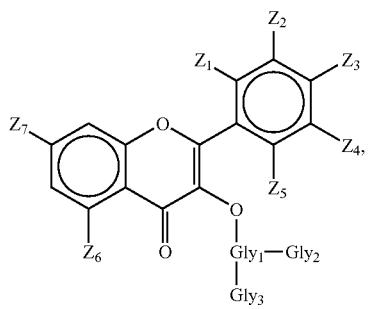

The flavone glycosides according to the invention are particularly advantageously from the group given by the following structure:

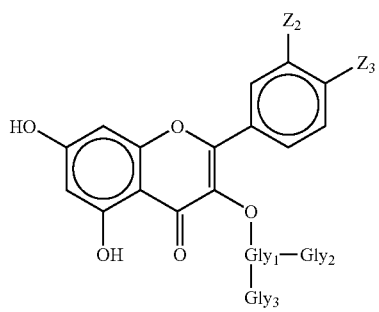

where $Gly_1$, $Gly_2$ and $Gly_3$, independently of one another, are monoglycoside radicals or. $Gly_2$ and $Gly_3$ can also, individually or together, represent saturations by hydrogen atoms.

Preferably, $Gly_1$, $Gly_2$ and $Gly_3$, independently of one another, are chosen from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, can also be used advantageously in some circumstances. It may also be advantageous according to the invention to use pentosyl radicals.

For the purposes of the present invention, it is particularly advantageous to choose the flavone glucoside(s) from the group consisting of α-glucosylrutin, α-glucosylmyricetin, α-glucosylisoquercitrin, α-glucosylisoquercetin and α-glucosylquercitrin.

Particular preference is given, according to the invention, to α-glucosylrutin.

Also advantageous according to the invention are naringin (aurantin, naringenin-7-rhamnoglucoside), hesperidin (3',5,7-trihydroxy-4'-methoxyflavanone-7-rutinoside, hesperidoside, hesperetin-7-O-rutinoside), rutin (3,3',4',5,7-pentahydroxyflyvone-3-rutinoside, quercetin-3-rutinoside, sophorin, birutan, rutabion, taururtin, phytomelin, melin), troxerutin (3,5-dihydroxy-3',4',7-tris(2-hydroxyethoxy)flavone-3-(6-O-(6-deoxy-α-L-man nopyranosyl)-β-D-glucopyranoside)), monoxerutin (3,3',4',5-tetrahydroxy-7-(2-hydroxyethoxy) flavone-3-(6-O-(6-deoxy-α-L-mannopyranosyl)-β-D-glucopyranoside)), dihydrorobinetin (3,3',4',5',7-pentahydroxyflavanone), taxifolin (3,3',4',5,7-pentahydroxyflavanone), eriodictyol-7-glucoside (3',4',5,7-tetrahydroxyflavanone-7 glucoside), flavanomarein (3',4',7,8-tetrahydroxyflavanone-7 glucoside) and isoquercetin (3,3',4',5,7-pentahydroxyflavanone-3-(β-D-glucopyranoside).

It is also advantageous to choose the active ingredient(s) from the group of ubiquinones and plastoquinones.

Ubiquinones are distinguished by the structural formula

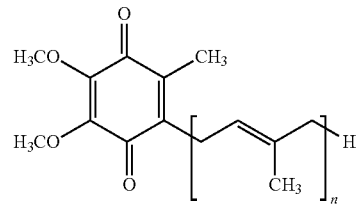

and are the most widespread and thus the most investigated bioquinones. Ubiquinones are referred to, depending on the number of isoprene units linked in the side chain, as Q-1, Q-2, Q-3 etc., or depending on the number of carbon atoms, as U-5, U-10, U-15 etc. They preferably appear with certain chain lengths, e.g. in some microorganisms and yeasts where n=6. In most mammals including man, Q10 predominates.

Coenzyme Q10 is particularly advantageous and is characterized by the following structural formula:

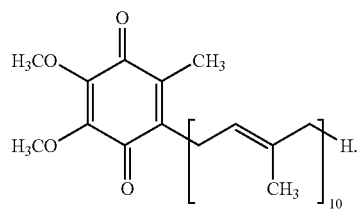

Plastoquinones have the general structural formula

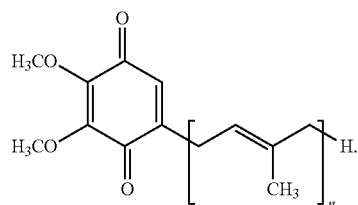

Plastoquinones differ in the number n of isoprene radicals and are referred to accordingly, e.g. PQ-9 (n=9). In addition, other plastoquinones with varying substituents on the quinone ring exist.

Creatine or creatine derivatives are also preferred active ingredients for the purposes of the present invention. Creatine is characterized by the following structure:

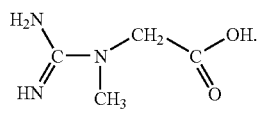

Preferred derivatives are creatine phosphate and creatine sulfate, creatine acetate, creatine ascorbate and the derivatives esterified at the carboxyl group with mono- or polyfunctional alcohols.

A further advantageous active ingredient is L-carnitine [3-hydroxy-4-(trimethylammonio)butyrobetaine]. Acylcarnitines which chosen from the group of substances of the following general structural formula

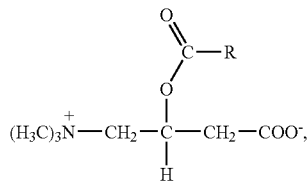

where R is chosen from the group of branched and unbranched alkyl radicals having up to 10 carbon atoms, are advantageous active ingredients for the purposes of the present invention. Preference is given to propionylcarnitine and, in particular, acetylcarnitine. Both enantiomers (D and L form) are to be used advantageously for the purposes of the present invention. It may also be advantageous to use any enantiomer mixtures, for example a racemate of D and L form.

Further advantageous active ingredients are pyridoxol, aminoguadin, phytochelatin, isoflavones (Genistein, Daidzein, Daidzin, Glycitin), niacin, tyrosine sulfate, dioic acid, adenosine, pyridoxine, arginin, vitamin K, biotin, aroma substances, α-glucosylrutin, tocopherol, lipoic acid, panthenol, tocopherol acetate, retinol, biotin, vitamin C, creatine, coenzyme Q10, 3-hydroxy-4-(trimethylammonio)butyrobetaine and sericoside.

The list of specified active ingredients or active ingredient combinations which can be used in the preparations according to the invention is not of course intended to be limiting. The active ingredients can be used individually or in any combinations with one another.

Advantageous active ingredients are also antioxidants, in particular those which can protect not only the constituents of the formulation, but also the skin, against oxidative stress. Particularly advantageous antioxidants are urocanic acid, carnosine, carotenoids, carotenes, lipoic acid, α-hydroxy fatty acids, α-hydroxy acids, and ubiquinone. The amount of antioxidants (one or more compounds) in the preparations is preferably 0.001 to 30% by weight, particularly preferably 0.05-20% by weight, in particular 1-10% by weight, based on the total weight of the preparation.

It is in some cases possible and advantageous to use the preparations according to the invention as bases for pharmaceutical formulations. Corresponding requirements apply mutatis mutandis in the formulation of medicinal preparations. The transitions between pure cosmetics and pure pharmaceuticals are fluid. Suitable pharmaceutical active ingredients according to the invention are, in principle, all active ingredient classes, preference being given to lipophilic active ingredients. Examples are: antihistamines, antiphlogistics, antibiotics, antimycotics, the active ingredients which promote circulation, keratolytics, antihistamines, antiphlogistics, antibiotics, antimycotics, the active ingredients which promote circulation, keratolytics, hormones, steroids, vitamins, hormones, steroids, vitamins, etc.

Particularly advantageous repellent active ingredients for the purposes of the present invention are the abovementioned active ingredients N,N-diethyl-3-methylbenzamide, ethyl 3-(N-n-butyl-N-acetylamino)propionate, 2-(2-hydroxyethyl)-1-methylpropyl 1-piperidinecarboxylate and dimethyl phthalate.

It is also possible to use additional substances to modify the consistency of the preparations according to the invention, for example thickeners, which can be chosen from the group of substances which carry at least two hydrophilic radicals which are bonded to one another via a hydrophobic group, thus conforming to the molecular schemes

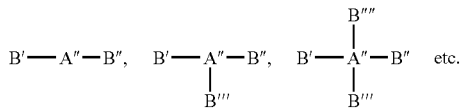

Here, the radicals B with the various indices represent hydrophilic groups, the radicals A with the various indices represent hydrophobic groups.

Such thickeners are preferably chosen from the group of triblock copolymers of the type

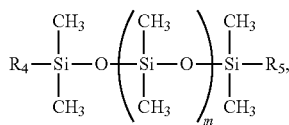

where m may be a number from 10 to 10000, $R_4$ and $R_5$ may be identical or different and are chosen from the group which is represented by the general structure

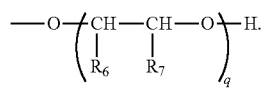

Here, $R_6$ and $R_7$ may, independently of one another, be chosen such that they can be H and methyl, but such that both radicals cannot be methyl at the same time. q is a number from 2 to 1000, preferably from 10 to 200.

$R_4$ and $R_5$ may also represent polyol radicals (e.g. glyceryl, polyglyceryl, sorbityl, cellulose radicals etc.).

Particularly when the preparations according to the invention are to be characterized by simple or easier ability to be washed off human skin, it is advantageous to incorporate water-soluble or water-swellable polymers, in particular cellulose or starch derivatives etherified with alkyl groups, into the preparations. β-glucans, xanthan gum, dextrans, hydroxymethylcellulose, hydroxyethylcellulose, hydroxypropylcellulose, methoxy-PEG-22/dodecyl glycol copolymers, and poloxamers are particularly advantageous.

Advantageous water-soluble or water-swellable polymers may also be chosen as hydrophilic starch esterified with one or more n-octenylsuccinate radicals. Such starch derivatives are characterized by the structure starch-$X_n$, where X symbolizes the radical

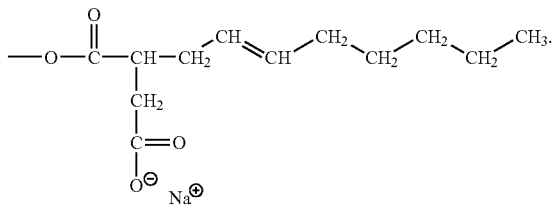

Starch derivatives to be used advantageously according to the invention still do not officially bear an INCI name (International Nomenclature Cosmetic Ingredient), it must bear the name "starch sodium octenyl succinate". Those products which are sold under the name Amiogum®, in particular Amiogum®23 from Cerestar US are particularly advantageous.

It is preferred to choose the content of water-soluble or water-swellable polymers in the concentration range from 0.01-5.0% by weight, particularly preferably 0.1-1.0% by weight.

The incorporation of such water-soluble or water-swellable polymers preferably takes place by incorporating them into the water phase and adding them, with the water phase, particularly preferably after complete dissolution or swelling, to the molten fatty phase of the preparations.

Also favorable are those cosmetic and dermatological preparations which are in the form of a sunscreen composition. Preferably, besides the active ingredient combinations according to the invention, these additionally comprise at least one UVA filter substance, at least one UVB filter substance or at least one inorganic pigment.

Preparations according to the invention advantageously comprise substances which absorb UV radiation in the UVB region, where the total amount of filter substances is, for example, 0.1% by weight to 30% by weight, preferably 0.5 to 10% by weight, in particular 1 to 6% by weight, based on the total weight of the preparations, in order to provide cosmetic or dermatological preparations which protect the skin from the entire range of ultraviolet radiation. They can also serve as sunscreen compositions.

Preferred inorganic pigments are metal oxides or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides.

For the purposes of the present invention, such pigments may advantageously be surface-treated ("coated"), the intention being, for example, to form or retain an amphiphilic or hydrophobic character. This surface treatment can consist in providing the pigments with a thin hydrophobic layer by processes known per se.

Advantageous according to the invention are, for example, titanium dioxide pigments which have been coated with octylsilanol. Suitable titanium dioxide particles are available under the trade name T805 from Degussa. Also particularly advantageous are $TiO_2$ pigments coated with aluminum stearate, e.g. those available under the trade name MT 100 T from TAYCA.

A further advantageous coating of the inorganic pigments consists of dimethylpolysiloxane (also: dimethicone), a mixture of completely methylated, linear siloxane polymers which have been terminally blocked by trimethylsiloxy units. Particularly advantageous for the purposes of the present invention are zinc oxide pigments which are coated in this way.

Also advantageous is a coating of the inorganic pigments with a mixture of dimethylpolysiloxane, in particular dimethylpolysiloxane with an average chain length of from 200 to 350 dimethylsiloxane units, and silica gel, which is also referred to as simethicone. In particular, it is advantageous for the inorganic pigments to be additionally coated with aluminum hydroxide or aluminum oxide hydrate (also: alumina, CAS No. 1333-84-2). Particularly advantageous are titanium dioxides which have been coated with simethicone and alumina, it also being possible for the coating to comprise water. One example thereof is the titanium dioxide available under the trade name Eusolex T2000 from Merck.

An advantageous organic pigment for the purposes of the present invention is 2,2'-methylenebis(6-(2H-benzotriazol-2-yl)-4-(1,1,3,3-tetramethylbutyl)phenol) [INCI: bisoctyltriazole], which is available under the trade name Tinosorb® M from CIBA-Chemikalien.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Further advantageous UV filter substances for the purposes of the present invention are so-called broadband filters, i.e. filter substances which absorb both UV-A and also UV-B radiation.

Advantageous broadband filters or UV-B filter surfactants are, for example, bisresorcinyltriazine derivatives. Particular preference is given to 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH.

For the purposes of the present invention, particularly advantageous preparations which are characterized by high or very high UV-A protection preferably comprise two or more UV-A or broadband filters, in particular dibenzoylmethane derivatives [for example 4-(tert-butyl)-4'-methoxydibenzoylmethane], benzotriazole derivatives [for example 2,2'-methylenebis(6-2H-benzotriazol-2-yl)-4-(1,1,3,3-tetramethylbutyl)phenol)], phenylene-1,4-bis(2-benzimidazyl)-3,3'-5,5'-tetrasulfonic acid or its salts, 1,4-di(2-oxo-10-sulfo-3-bornylidenemethyl)benzene or salts thereof or 2,4-bis{[4-(2-ethylhexyloxy)-2-hydroxy]phenyl}-6-(4-methoxyphenyl)-1,3,5-triazine, in each case individually or in any combinations with one another.

Other UV filter substances, which have the structural formula

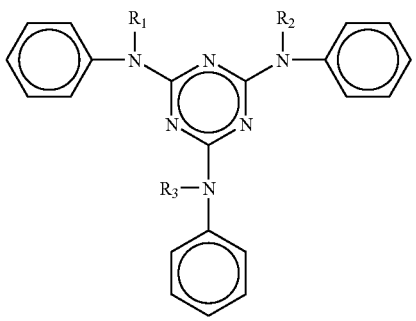

are also advantageous UV filter substances for the purposes of the present invention, for example the s-triazine derivatives described in European laid-open specification EP 570 838 A1, whose chemical structure is expressed by the generic formula

[Structure diagram]

where
R is a branched or unbranched $C_1$-$C_{18}$-alkyl radical, a $C_5$-$C_{12}$-cycloalkyl radical, optionally substituted with one or more $C_1$-$C_4$-alkyl groups, X is an oxygen atom or an NH group, $R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

[Structure diagram: A—[O—CH$_2$—CH(R$_3$)]$_n$—]

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, $R_2$ is a branched or unbranched $C_1$-$C_{18}$-alkyl radical, a $C_5$-$C_{12}$-cycloalkyl radical, optionally substituted by one or more $C_1$-$C_4$-alkyl groups, when X is the NH group, and a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

[Structure diagram: A—[O—CH$_2$—CH(R$_3$)]$_n$—]

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, when X is an oxygen atom.

A particularly preferred UV filter substance for the purposes of the present invention is also an unsymmetrically substituted s-triazine, the chemical structure of which is expressed by the formula

[Structure diagram]

and which is also referred to below as dioctylbutylamidotriazone (INCI: Dioctylbutamidotriazone), and is available under the trade name UVASORB HEB from Sigma 3V.

Also advantageous for the purposes of the present invention is a symmetrically substituted s-triazine, tris(2-ethylhexyl) 4,4',4''-(1,3,5-triazine-2,4,6-triyltriimino)tris-benzoate, synonym: 2,4,6-tris[anilino-(p-carbo-2'-ethyl-1'-hexyloxy)]-1,3,5-triazine (I NCI: Octyl Triazone), which is marketed by BASF Aktiengesellschaft under the trade name UVINUL® T 150.

European laid-open specification 775 698 also describes preferred bisresorcinyltriazine derivatives, the chemical structure of which is expressed by the generic formula

[Structure diagram]

where $R_1$, $R_2$ and $A_1$ represent very different organic radicals.

Also advantageous for the purposes of the present invention are 2,4-bis{[4-(3-sulfonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2''-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2''-methylpropyloxy)-2-hydroxy]phenyl}-6-(4-methoxyphenyl)-1,3,5-triazine.

An advantageous broadband filter for the purposes of the present invention is 2,2'-methylenebis(6-(2H-benzotriazol-2- yl)-4-(1,1,3,3-tetramethylbutyl)phenol), which is available under the trade name Tinosorb® M from CIBA-Chemikalien GmbH.

Another advantageous broadband filter for the purposes of the present invention is 2-(2H-benzotriazol-2-yl)-4-methyl-6-[2-methyl-3-[1,3,3,3-tetramethyl-1-[(trimethylsilyl)-oxy]disiloxanyl]propyl]phenol (CAS No. 155633-54-8) having the INCI name Drometrizole Trisiloxane.

The UV-B or broadband filters can be oil-soluble or water-soluble. Examples of advantageous oil-soluble UV-B or broadband filter substances are:

- 3-benzylidenecamphor derivatives, preferably 3-(4-methylbenzylidene)camphor, 3-benzylidenecamphor;
- 4-aminobenzoic acid derivatives, preferably 2-ethylhexyl 4-(dimethylamino)-benzoate, amyl 4-(dimethylamino)benzoate;
- 2,4,6-trianilino(p-carbo-2'-ethyl-1'-hexyloxy)-1,3,5-triazine;
- esters of benzalmalonic acid, preferably di(2-ethylhexyl) 4-methoxybenzalmalonate,
- esters of cinnamic acid, preferably 2-ethylhexyl 4-methoxycinnamate, isopentyl 4-methoxycinnamate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone
- 3-(4-(2,2-bisethoxycarbonylvinyl)phenoxy)propenyl)methoxysiloxane/dimethylsiloxane copolymer which is available, for example, under the trade name Parsol® SLX from Hoffmann La Roche, and
- UV filters bonded to polymers.

Examples of advantageous water-soluble UV-B or broadband filter substances are:

- salts of 2-phenylbenzimidazole-5-sulfonic acid, such as its sodium, potassium or its triethanolammonium salt, and also the sulfonic acid itself;
- sulfonic acid derivatives of 3-benzylidenecamphor, such as, for example, 4-(2-oxo-3-bornylidenemethyl)benzenesulfonic acid, 2-methyl-5-(2-oxo-3-bornyl idenemethyl)sulfonic acid and salts thereof.
- phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name Bisimidazylate (CAS No. 180898-37-7), which is available, for example, under the trade name Neo Heliopan AP from Haarmann & Reimer;
- further advantageous UV-A filter substances are phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic bis-sodium salt with the INCI name Bisimidazylate, which is available, for example, under the trade name Neo Heliopan AP from Haarmann & Reimer, and 1,4-di(2-oxo-10-sulfo-3-bornylidenemethyl)benzene (also: 3,3'-(1,4-phenylenedimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di (2-oxo-3-bornylidenemethyl-10-sulfonic acid) has the INCI name Terephthalidene Dicamphor Sulfonic Acid (CAS No. 90457-82-2) and is available, for example, under the trade name Mexoryl SX from Chimex;

Another advantageous broadband filter for the purposes of the present invention is 2-(2H-benzotriazol-2-yl)-4-methyl-6-[2-methyl-3-[1,3,3,3-tetramethyl-1-[(trimethylsilyl)-oxy]disiloxanyl]propyl]phenol (CAS No. 155633-54-8) with the INCI name Drometrizole Trisiloxane, which is available under the trade name Mexory® XL from Chimex.

A further photoprotective filter substance to be used advantageously according to the invention is ethylhexyl 2-cyano-3,3-diphenylacrylate (octocrylene), which is available from BASF under the name Uvinul® N 539.

It may also be of considerable advantage to use polymer-bound or polymeric UV filter substances in preparations according to the present invention, in particular those described in WO-A-92/20690.

In some instances, it may also be advantageous to incorporate further UV-A or UV-B filters in accordance with the invention into cosmetic or dermatological preparations, for example certain salicylic acid derivatives, such as 4-isopropylbenzyl salicylate, 2-ethylhexyl salicylate (=octyl salicylate) and homomenthyl salicylate.

The list of given UV filters which can be used for the purposes of the present invention is not of course intended to be limiting.

In addition, in some instances, it may be advantageous to incorporate film formers into the cosmetic or dermatological preparations according to the invention, for example in order to improve the water resistance of the preparations or to increase the UV protection power (UV-A or UV-B boosting). Both water-soluble or dispersible, and also fat-soluble film formers are suitable, in each case individually or in combination with one another.

Advantageous water-soluble or dispersible film formers are, for example, polyurethanes (e.g. the Avalure® grades from Goodrich), dimethicone copolyol polyacrylates (Silsoft Surface® from Witco Organo Silicones Group), PVPNA (VA=vinyl acetate) copolymer (Luviscol VA 64 Powder from BASF), etc.

Advantageous fat-soluble film formers are, for example, the film formers from the group of polymers based on polyvinylpyrrolidone (PVP)

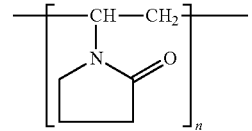

Particular preference is given to copolymers of polyvinylpyrrolidone, for example the PVP hexadecene copolymer and the PVP eicosen copolymer, which are available under the trade names Antaron V216 and Antaron V220 from GAF Chemicals Cooperation, and also tricontayl PVP and the like.

Emulsions according to the invention may also comprise powder substances. The powder substances used are, for example, bismuth oxychloride, titanized mica, silicon dioxide (fumed silica), spherical silicon dioxide beads, polymethyl methacrylate beads, micronized Teflon, boron nitride, acrylate polymers, aluminum silicate, aluminum starch octenylsuccinate, bentonite, calcium silicate, cellulose, chalk, corn starch, glyceryl starch, hectorite, hydrated silica, kaolin, magnesium hydroxides, magnesium oxide, magnesium silicates, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, aluminum oxide, attapulgite, calcium carbonate, calcium silicate, dextran, kaolin, nylon, silica silylate, silk powder, serecite, tin oxide, titanium hydroxide, trimagnesium phosphate, walnut shell powder or any mixtures.

The customary constituents of cosmetic sticks can additionally advantageously be incorporated into the preparations according to the invention, e.g. the customary auxiliaries and additives, such as perfume oils, preservatives, color pigments, photoprotective agents, stabilizers.

The person skilled in the art is of course aware that high-quality cosmetic preparations are in most cases inconceivable without customary auxiliaries and additives. These include, for example, consistency-imparting agents, fillers, perfume, additional active ingredients, such as vitamins or proteins, insect repellents, alcohol, water, salts, and antimicrobially, proteolytically or keratolytically effective substances etc.

EXAMPLES

Unless stated otherwise, all amounts, percentages or parts refer to the weight, in particular to the total weight of the preparations or of the particular mixtures. The examples below are intended to explain the invention without limiting it.

Example 1

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Cetearyl isononanoate | 14.70 |
| Ubiquinone (cyclodextrin encapsulated) | 0.20 |
| Ubiquinone | 0.20 |
| Biotin | 0.20 |
| Concealing pigments | 1.50 |
| $C_{20-40}$-Alkyl stearate | 9.00 |
| Glycerol | 10.00 |
| Perfume | 0.30 |
| Preservative | 0.58 |
| Water | ad 100.00 |

Example 2

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| Ubiquinone (cyclodextrin encapsulated) | 0.20 |
| Ubiquinone | 0.20 |
| Biotin | 0.20 |
| Concealing pigments | 1.50 |
| $C_{20-40}$-Alkyl stearate | 9.00 |
| Glycerol | 10.00 |
| Perfume | 0.30 |
| Preservative | 0.58 |
| Water | ad 100.00 |

Example 3

| Prophylactically effective against wrinkles or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 5.70 |
| Ubiquinone (cyclodextrin encapsulated) | 0.20 |
| Ubiquinone | 0.20 |
| Biotin | 0.20 |
| Concealing pigments | 10.00 |
| $C_{20-40}$-Alkyl stearate | 9.00 |
| Glycerol | 10.00 |
| Octyldodecanol | 5.70 |
| Dicaprylyl ether | 5.70 |
| Shea butter | 1.00 |
| Jojoba oil | 1.00 |
| Perfume | 0.30 |
| Preservative | 0.58 |
| Water | ad 100.00 |

Example 4

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 5.70 |
| Ubiquinone (cyclodextrin encapsulated) | 0.20 |
| Ubiquinone | 0.20 |
| Biotin | 0.20 |
| Concealing pigments | 10.00 |
| $C_{20-40}$-Alkyl stearate | 9.00 |
| Glycerol | 10.00 |
| Octyldodecanol | 5.70 |
| Dicaprylyl ether | 5.70 |
| Shea butter | 1.00 |
| Jojoba oil | 1.00 |
| Perfume | 0.30 |
| Preservative | 0.58 |
| Water | ad 100.00 |

Example 5

| Prophylactically effective or antiwrinkle stick with a high water and moisturizer content | |
|---|---|
| | % by wt. |
| PEG-45/dodecyl glycol copolymer | 2.00 |
| Polyglyceryl-3 diisostearate | 2.40 |
| PEG-8 beeswax | 1.00 |
| Octyldodecanol | 10.75 |
| Squalene | 1.00 |
| Ubiquinone (cyclodextrin encapsulated) | 0.20 |
| Ubiquinone | 0.20 |
| Biotin | 0.20 |
| Concealing pigments | 10.00 |
| $C_{20-40}$-Alkyl stearate | 8.00 |
| Glycerol | 10.00 |
| Jojoba oil | 1.00 |
| Perfume | 0.30 |
| Preservative | 0.58 |
| Water | ad 100.00 |

Example 6

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| $C_{20-40}$-Alkyl stearate | 9.00 |
| Ascorbic acid | 3.00 |
| Glycerol | 10.00 |
| Perfume | 0.30 |
| Preservative | 0.58 |
| Water | ad 100.00 |

Example 7

| Prophylactically effective or antiwrinkle stick with a high water and moisturizer content | |
|---|---|
| | % by wt. |
| PEG-45/dodecyl glycol copolymer | 1.80 |
| Polyglyceryl-3 diisostearate | 2.70 |
| PEG-8 beeswax | 1.10 |
| Octyldodecanol | 5.90 |
| Squalane | 1.00 |
| Castor oil | 3.00 |
| Jojoba oil | 1.00 |
| Avocado oil | 1.50 |
| Macadamia oil | 1.50 |
| Hydrogenated polydecene | 4.24 |
| Tocopherol acetate | 1.10 |
| Cetyl palmitate | 1.10 |
| Ubiquinone (cyclodextrin encapsulated) | 0.20 |
| Lipoic acid | 0.20 |
| Biotin | 0.20 |
| Concealing pigments | 11.50 |
| bis-Ethylhexyloxyphenol methoxyphenyltriazine | 1.00 |
| Ethylhexyltriazone | 1.00 |
| Glycerol | 7.50 |
| Perfume | 0.30 |
| Preservative | 0.58 |
| Water | ad 100.00 |

Example 8

| Prophylactically effective or antiwrinkle stick with a high water and moisturizer content | |
|---|---|
| | % by wt. |
| PEG-45/dodecyl glycol copolymer | 1.80 |
| Polyglyceryl-3 diisostearate | 2.70 |
| PEG-8 beeswax | 1.10 |
| Octyldodecanol | 5.90 |
| Squalane | 1.00 |
| Castor oil | 3.00 |
| Jojoba oil | 1.00 |
| Avocado oil | 1.50 |
| Macadamia oil | 1.50 |
| Hydrogenated polydecene | 4.24 |
| Tocopherol acetate | 1.10 |
| Cetyl palmitate | 1.10 |
| Ubiquinone (cyclodextrin encapsulated) | 0.20 |
| Caruithine | 0.20 |
| Biotin | 0.20 |
| Concealing pigments | 11.50 |
| bis-Ethylhexyloxyphenol methoxyphenyltriazine | 1.00 |
| Ethylhexyltriazone | 1.00 |
| Glycerol | 7.50 |
| Perfume | 0.30 |
| Preservative | 0.58 |
| Water | ad 100.00 |

Example 9

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| $C_{20-40}$-Alkyl stearate | 9.00 |
| Tocopherol | 3.00 |
| Glycerol | 10.00 |
| Perfume | 0.30 |
| Preservative | 0.58 |
| Water | ad 100.00 |

Example 10

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| $C_{18-36}$-Acid triglyceride | 1.00 |
| $C_{20-40}$-Alkyl stearate | 9.00 |
| α-Glucosylrutin, creatine (1:1) | 0.50 |
| Glycerol, Fucogel (9:1) | 10.00 |
| Preservative | 0.58 |
| Water | ad 100.00 |

Example 11

| Prophylactically effective or antiwrinkle stick with a high water and moisturizer content | |
|---|---|
| | % by wt. |
| PEG-45/dodecyl glycol copolymer | 1.60 |
| Sorbitan isostearate | 1.60 |
| Caprylic/capric triglyceride | 14.70 |
| $C_{18-36}$-Acid triglyceride | 1.00 |
| $C_{20-40}$-Alkyl stearate | 9.00 |
| Glycerol, glycine (9:1) | 10.00 |
| Preservative | 0.58 |
| Water | ad 100.00 |

Example 12

| Prophylactically effective against wrinkles or antiwrinkle stick with a high water and moisturizer content | |
|---|---|
| | % by wt. |
| PEG-45/dodecyl glycol copolymer | 1.80 |
| PEG-30 dipolyhydroxystearate | 2.70 |
| PEG-8 beeswax | 1.10 |
| Octyldodecanol | 5.90 |
| Squalane | 1.00 |
| Castor oil | 3.00 |
| Jojoba oil | 1.00 |
| Avocado oil | 1.50 |
| Macadamia oil | 1.50 |
| Hydrogenated polydecene | 4.24 |
| Tocopherol acetate | 1.10 |
| Cetyl palmitate | 1.10 |
| Ubiquinone (cyclodextrin encapsulated) | 0.20 |
| Methyl palmitate | 1.00 |
| Biotin | 0.20 |
| Concealing pigments | 11.50 |
| bis-Ethylhexyloxyphenol methoxyphenyltriazine | 1.00 |
| Ethylhexyltriazone | 1.00 |
| Glycerol, lactic acid (9:1) | 7.50 |
| Perfume | 0.30 |
| Preservative | 0.58 |
| Water | ad 100.00 |

Example 13

| Prophylactically effective or antiwrinkle stick with a high water and moisturizer content | |
|---|---|
| | % by wt. |
| PEG-45/dodecyl glycol copolymer | 1.60 |
| Polyglyceryl-3 methylglucose distearate | 1.60 |
| Cetearyl isononanoate | 14.70 |
| Ubiquinone (cyclodextrin encapsulated) | 0.20 |
| Ubiquinone | 0.20 |
| Tocopherol | 0.20 |
| Concealing pigments | 1.50 |
| $C_{20-40}$-Alkyl stearate | 9.00 |
| Glycerol, butylene glycol (9:1) | 10.00 |
| Perfume | 0.30 |
| Preservative | 0.58 |
| Water | ad 100.00 |

Example 14

| Prophylactically effective or antiwrinkle stick with a high water and moisturizer content | |
|---|---|
| | % by wt. |
| PEG-45/dodecyl glycol copolymer | 1.60 |
| Propylene glycol isostearate | 1.60 |
| Cetearyl isononanoate | 14.70 |
| Ubiquinone (cyclodextrin encapsulated) | 0.20 |
| Ubiquinone | 0.20 |
| Tocopherol | 0.20 |
| Concealing pigments | 1.50 |
| $C_{20-40}$-Alkyl stearate | 9.00 |
| Glycerol, NaCl | 10.00 |
| Perfume | 0.30 |
| Preservative | 0.58 |
| Water | ad 100.00 |

Example 15

| Prophylactically effective or antiwrinkle stick with a high water and moisturizer content | |
|---|---|
| | % by wt. |
| PEG-45/dodecyl glycol copolymer | 2.00 |
| Glycerol isostearate | 2.40 |
| PEG-8 beeswax | 1.00 |
| Octyldodecanol | 10.75 |
| Squalene | 1.00 |
| Ubiquinone (cyclodextrin encapsulated) | 0.20 |
| Ubiquinone | 0.20 |
| Biotin | 0.20 |
| Concealing pigments | 10.00 |
| $C_{20-40}$-Alkyl stearate | 8.00 |
| Glycerol | 10.00 |
| Jojoba oil | 1.00 |
| Perfume | 0.30 |
| Preservative | 0.58 |
| Water | ad 100.00 |

Example 16

| Prophylactically effective or antiwrinkle stick with a high water and moisturizer content | |
|---|---|
| | % by wt. |
| PEG-45/dodecyl glycol copolymer | 1.80 |
| Polyglyceryl-3 diisostearate | 2.70 |
| PEG-8 beeswax | 1.10 |
| Octyldodecanol | 5.90 |
| Squalane | 1.00 |
| Castor oil | 3.00 |
| Jojoba oil | 1.00 |
| Avocado oil | 1.50 |
| Macadamia oil | 1.50 |
| Hydrogenated polydecene | 4.24 |
| Tocopherol acetate | 1.10 |
| Cetyl palmitate | 1.10 |
| Ubiquinone (cyclodextrin encapsulated) | 0.20 |
| Carnithine | 0.20 |
| Biotin | 0.20 |
| Concealing pigments | 11.50 |
| Butylmethoxydibenzoylmethane | 1.00 |
| 4-Methylbenzylidene camphor | 1.00 |
| Glycerol, sodium pyrrolidonecarboxylic acid salt (9:1) | 7.50 |
| Perfume | 0.30 |
| Preservative | 0.58 |
| Water | ad 100.00 |

Example 17

| Prophylactically effective or antiwrinkle stick with a high water and moisturizer content | |
|---|---|
| | % by wt. |
| PEG-45/dodecyl glycol copolymer | 1.80 |
| Polyglyceryl-3 diisostearate | 2.70 |
| PEG-8 beeswax | 1.10 |
| Octyldodecanol | 5.90 |
| Squalane | 1.00 |
| Castor oil | 3.00 |
| Jojoba oil | 1.00 |
| Avocado oil | 1.50 |
| Macadamia oil | 1.50 |
| Hydrogenated polydecene | 4.24 |
| Tocopherol acetate | 1.10 |
| Cetyl palmitate | 1.10 |
| Ubiquinone (cyclodextrin encapsulated) | 0.20 |
| Biotin | 0.20 |
| Concealing pigments | 11.50 |
| Octocrylene | 1.00 |
| 4-Methylbenzylidene camphor | 1.00 |
| Glycerol, hyaluronic acid salt (9:1) | 7.50 |
| Perfume | 0.30 |
| Preservative | 0.58 |
| Water | ad 100.00 |

Example 18

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| $C_{20-40}$-Alkyl stearate | 9.00 |
| Tocopherol | 3.00 |
| Retinol | 0.20 |
| Phenylene-1,4-bis(2-benzimidazyl)-3,3'-5,5'-tetrasulfonic acid bis-sodium salt | 3.00 |
| Dioctylbutamidotriazone | 3.00 |
| Glycerol, polyethylene glycol (9:1) | 10.00 |
| Perfume | 0.30 |
| Preservative | 0.58 |
| Water | ad 100.00 |

Example 19

| Prophylactically effective or antiwrinkle stick with a high water and moisturizer content | |
|---|---|
| | % by wt. |
| PEG-45/dodecyl glycol copolymer | 1.60 |
| Polyglyceryl-3 diisostearate | 1.60 |
| Caprylic/capric triglyceride | 14.70 |
| $C_{18-36}$-Acid triglyceride | 1.00 |
| $C_{20-40}$-Alkyl stearate | 9.00 |
| α-Glucosylrutin, creatine (1:1) | 0.50 |
| Ethylhexyltriazone | 2.00 |
| Phenylbenzimidazolesulfonic acid salt | 1.00 |
| Glycerol, Fucogel (9:1) | 10.00 |
| Preservative | 0.58 |
| Water | ad 100.00 |

Example 20

| Prophylactically effective or antiwrinkle stick with a high water and moisturizer content | |
|---|---|
| | % by wt. |
| PEG-45/dodecyl glycol copolymer | 2.00 |
| Glycerol isostearate | 2.40 |
| PEG-8 beeswax | 1.00 |
| Ethylhexyl salicylate | 2.00 |
| Octyldodecanol | 10.75 |
| Squalene | 1.00 |
| Ubiquinone (cyclodextrin encapsulated) | 0.20 |
| Ubiquinone | 0.20 |
| Biotin | 0.20 |
| Concealing pigments | 10.00 |
| $C_{20-40}$-Alkyl stearate | 8.00 |
| Glycerol, urea (9:1) | 10.00 |
| Jojoba oil | 1.00 |
| Perfume | 0.30 |
| Preservative | 0.58 |
| Water | ad 100.00 |

Example 21

Antiacne stick

| | % by wt. |
|---|---|
| Cetearyl isononanoate | 15.00 |
| PEG-45/dodecyl glycol copolymer | 1.60 |
| Polyglyceryl-3 diisostearate | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 22

Antiacne stick

| | % by wt. |
|---|---|
| Cetearyl isononanoate | 15.00 |
| PEG-45/dodecyl glycol copolymer | 1.60 |
| Polyglyceryl-3 diisostearate | 1.60 |
| Lactic acid | 3.00 |
| Salicylic acid | 0.50 |
| Zinc sulfate | 0.70 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 23

Antiacne stick

| | % by wt. |
|---|---|
| Cetearyl isononanoate | 15.00 |
| PEG-45/dodecyl glycol copolymer | 1.60 |
| Polyglyceryl-3 diisostearate | 1.60 |
| Lactic acid | 3.00 |
| Salicylic acid | 0.50 |
| Polyaminopropyl biguanide | 1.00 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 24

Antiacne stick

| | % by wt. |
|---|---|
| Cetearyl isononanoate | 15.00 |
| PEG-45/dodecyl glycol copolymer | 1.60 |
| Polyglyceryl-3 diisostearate | 1.60 |
| Aluminum chlorohydrate | 4.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 25

Antiacne stick

| | % by wt. |
|---|---|
| Polyglyceryl-3 diisostearate | 1.60 |
| PEG-45/dodecyl glycol copolymer | 1.60 |
| Glyceryl caprate | 0.50 |
| Polyglyceryl-3 caprylate | 0.50 |
| Caprylic/capric triglyceride | 4.00 |
| Octyldodecanol | 4.00 |
| Dicaprylyl ether | 4.00 |
| Cetearyl behenate | 6.00 |
| Lactic acid | 2.00 |
| Octacosanyl stearate | 8.00 |
| Glycerol | 10.00 |
| Water | ad 100.00 |

Example 26

Antiacne stick

| | % by wt. |
|---|---|
| Polyglyceryl-3 diisostearate | 1.60 |
| PEG-45/dodecyl glycol copolymer | 1.60 |
| Glyceryl caprate | 3.00 |
| Caprylic/capric triglyceride | 4.00 |
| Octyldodecanol | 4.00 |
| Dicaprylyl carbonate | 4.00 |
| Cetearyl behenate | 6.00 |
| Salicylic acid | 1.00 |
| Octacosanyl stearate | 6.00 |
| Glycerol | 10.00 |
| Water | ad 100.00 |

Example 27

| Antiacne stick | |
|---|---|
| | % by wt. |
| Cetearyl isononanoate | 15.00 |
| PEG-45/dodecyl glycol copolymer | 1.60 |
| Polyglyceryl-3 diisostearate | 1.60 |
| Lactic acid | 2.00 |
| Salicylic acid | 0.50 |
| Citric acid | 1.00 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 28

| Antiacne stick | |
|---|---|
| | % by wt. |
| Cetearyl isononanoate | 15.00 |
| PEG-45/dodecyl glycol copolymer | 1.60 |
| Polyglyceryl-3 diisostearate | 1.60 |
| Lactic acid | 3.00 |
| Salicylic acid | 0.50 |
| 2-Ethylhexyl glycerol ether | 1.00 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 29

| Antiacne stick | |
|---|---|
| | % by wt. |
| Cetearyl isononanoate | 15.00 |
| PEG-45/dodecyl glycol copolymer | 1.60 |
| Polyglyceryl-3 diisostearate | 1.60 |
| Lactic acid | 2.00 |
| Salicylic acid | 0.50 |
| Citric acid | 1.00 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 30

| Antiacne stick | |
|---|---|
| | % by wt. |
| Cetearyl isononanoate | 15.00 |
| PEG-45/dodecyl glycol copolymer | 1.60 |
| Polyglyceryl-3 diisostearate | 1.60 |
| Sorbitan isostearate | 1.60 |
| Lactic acid | 2.00 |
| Salicylic acid | 0.50 |
| Citric acid | 1.00 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 31

| Antiacne stick | |
|---|---|
| | % by wt. |
| Cetearyl isononanoate | 15.00 |
| PEG-45/dodecyl glycol copolymer | 1.60 |
| PEG-30 dipolyhydroxystearate | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Methyl palmitate | 1.00 |
| Glycerol | 10.00 |
| Preservative | 0.50 |
| Water | ad 100.00 |

Example 32

| Antiacne stick | |
|---|---|
| | % by wt. |
| Cetearyl isononanoate | 15.00 |
| PEG-45/dodecyl glycol copolymer | 1.60 |
| Polyglyceryl-2 dipolyhydroxystearate | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 33

| Antiacne stick | |
|---|---|
| | % by wt. |
| Cetearyl isononanoate | 15.00 |
| PEG-45/dodecyl glycol copolymer | 1.60 |
| PEG-40 sorbitan perisostearate | 1.60 |

-continued

| Antiacne stick | |
|---|---|
| | % by wt. |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol, sodium pyrrolidonecarboxylic acid salt 10:1 | 10.00 |
| Preservative | 0.50 |
| Water | ad 100.00 |

Example 34

| Antiacne stick | |
|---|---|
| | % by wt. |
| Cetearyl isononanoate | 15.00 |
| PEG-45/dodecyl glycol copolymer | 1.60 |
| Cetyl alcohol | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol, hyaluronic acid 10:1 | 10.00 |
| Preservative | 0.50 |
| Water | ad 100.00 |

Example 35

| Antiacne stick | |
|---|---|
| | % by wt. |
| Cetearyl isononanoate | 15.00 |
| PEG-45/dodecyl glycol copolymer | 1.60 |
| Propylene glycol isostearate | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| Glycerol, NMF 10:1 | 10.00 |
| Preservative | 0.50 |
| Water | ad 100.00 |

Example 36

| Antiacne stick | |
|---|---|
| | % by wt. |
| Cetearyl isononanoate | 15.00 |
| PEG-45/dodecyl glycol copolymer | 1.60 |
| Steareth-2 | 1.60 |
| Lactic acid | 3.00 |
| Salicylic acid | 0.50 |
| Concealing pigment mixture | 10.00 |

-continued

| Antiacne stick | |
|---|---|
| | % by wt. |
| Sodium hydroxide solution (10% strength) | 6.70 |
| $C_{20-40}$-Alkyl stearate | 8.00 |
| PEG-8 beeswax | 1.00 |
| Behenyl behenate | 0.50 |
| Glycerol, urea 10:1 | 10.00 |
| Preservative | 0.50 |
| Water | ad 100.00 |

Example 37

| Antiacne stick | |
|---|---|
| | % by wt. |
| Cetearyl isononanoate | 15.00 |
| PEG-45/dodecyl glycol copolymer | 1.60 |
| Polyglyceryl-3 methylglucose distearate | 1.60 |
| Lactic acid | 3.00 |
| Salicylic acid | 0.50 |
| Concealing pigment mixture | 10.00 |
| Sodium hydroxide solution (10% strength) | 6.70 |
| $C_{20-40}$-Alkyl stearate | 8.00 |
| $C_{18-36}$-Acid triglyceride | 1.00 |
| Glycerol, Fucogel 10:1 | 10.00 |
| Preservative | 0.50 |
| Water | ad 100.00 |

Example 38

| Antiacne stick as concealer | |
|---|---|
| | % by wt. |
| Cetearyl isononanoate | 15.00 |
| PEG-45/dodecyl glycol copolymer | 1.60 |
| Polyglyceryl-3 diisostearate | 1.60 |
| Lactic acid | 3.00 |
| 2-Butyloctanoic acid | 0.50 |
| Concealing pigment mixture | 10.00 |
| Sodium hydroxide solution (10% strength) | 6.70 |
| $C_{20-40}$-Alkyl stearate | 8.00 |
| Glycerol | 10.00 |
| Preservative | 0.50 |
| Water | ad 100.00 |

Example 39

| Decorative lipstick | |
|---|---|
| | % by wt. |
| PEG-45/dodecyl glycol copolymer | 1.60 |
| Polyglyceryl-3 diisostearate | 2.40 |
| Simethicone | 0.50 |
| Octyldodecanol | 4.00 |
| Polydecene | 4.80 |
| Castor oil | 5.00 |
| Ethylhexyl cocoate | 4.80 |

-continued

Decorative lipstick

| | % by wt. |
|---|---|
| *Buxus chinensis* | 1.00 |
| Squalane | 1.00 |
| PEG-8 beeswax | 1.00 |
| Butylmethoxydibenzoylmethane | 0.80 |
| 4-Methylbenzylidenecamphor | 1.60 |
| $C_{20-40}$-Alkyl stearate | 8.00 |
| Glycerol | 10.00 |
| Color paste | 11.60 |
| Perfume | 0.30 |
| Active ingredients | 1.10 |
| Preservative | 0.58 |
| Water | ad 100.00 |

Example 40

Foundation stick

| | % by wt. |
|---|---|
| PEG-45/dodecyl glycol copolymer | 1.60 |
| Polyglyceryl-3 diisostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| *Candelilla cera* | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 41

Decorative lipstick

| | % by wt. |
|---|---|
| PEG-45/dodecyl glycol copolymer | 1.600 |
| Polyglyceryl-3 diisostearate | 2.40 |
| Simethicone | 0.50 |
| Octyldodecanol | 3.20 |
| Polydecene | 4.80 |
| Castor oil | 5.00 |
| Dicaprylyl carbonate | 4.80 |
| *Buxus chinensis* | 1.00 |
| Squalane | 1.00 |
| Hydroxyethylcellulose | 0.30 |
| Butylmethoxydibenzoylmethane | 0.80 |
| 4-Methylbenzylidenecamphor | 1.60 |
| $C_{20-40}$-Alkyl stearate | 9.50 |
| Glycerol | 10.00 |
| Color paste | 11.60 |
| Perfume | 0.30 |
| Active ingredients | 1.10 |
| Preservative | 0.58 |
| Water | ad 100.00 |

Example 42

Lipstick

| | % by wt. |
|---|---|
| PEG-45/dodecyl glycol copolymer | 1.60 |
| Polyglyceryl-3 diisostearate | 2.40 |
| Simethicone | 0.50 |
| Polydecene | 4.80 |
| Castor oil | 5.00 |
| Dicaprylyl carbonate | 4.80 |
| *Buxus chinensis* | 1.00 |
| Squalane | 1.00 |
| Triisostearin | 3.50 |
| Butylmethoxydibenzoylmethane | 0.80 |
| 4-Methylbenzylidenecamphor | 1.60 |
| $C_{20-40}$-Alkyl stearate | 9.50 |
| Glycerol | 10.00 |
| Color paste | 11.60 |
| Perfume | 0.30 |
| Active ingredients | 1.10 |
| Preservative | 0.58 |
| Water | ad 100.00 |

Example 43

Decorative lipstick

| | % by wt. |
|---|---|
| PEG-45/dodecyl glycol copolymer | 1.60 |
| Polyglyceryl-3 diisostearate | 2.40 |
| Simethicone | 0.50 |
| Polydecene | 4.80 |
| Octyldodecanol | 5.00 |
| Castor oil | 3.00 |
| *Persea gratissima* | 1.50 |
| *Macadamia ternifolia* | 1.50 |
| *Buxus chinensis* | 1.00 |
| Squalane | 1.00 |
| Ethylhexyl methoxycinnamate | 2.00 |
| bis-Ethylhexyloxyphenol methoxyphenyltriazine | 0.25 |
| $C_{20-40}$-Alkyl stearate | 8.00 |
| Cetyl palmitate | 1.00 |
| PEG-8 beeswax | 1.00 |
| Glycerol | 7.50 |
| Pearl pigment | 2.00 |
| Color paste | 14.00 |
| Perfume | 0.30 |
| Active ingredients | 1.10 |
| Preservative | 0.58 |
| Water | ad 100.00 |

Example 44

Decorative lipstick

| | % by wt. |
|---|---|
| PEG-45/dodecyl glycol copolymer | 1.60 |
| Polyglyceryl-3 diisostearate | 2.40 |
| Simethicone | 0.50 |
| Octyldodecanol | 7.00 |
| Polydecene | 4.80 |

Example 45

Decorative lipstick

| | % by wt. |
|---|---|
| Castor oil | 3.00 |
| *Buxus chinensis* | 1.00 |
| Squalane | 1.00 |
| *Macadamia* oil | 1.50 |
| *Persea gratissima* | 1.50 |
| Ethylhexyl methoxycinnamate | 2.00 |
| bis-Ethylhexyloxyphenol methoxyphenyltriazine | 0.25 |
| Cetyl palmitate | 1.00 |
| $C_{20-40}$-Alkyl stearate | 8.00 |
| Glycerol | 7.50 |
| Color paste | 11.60 |
| Perfume | 0.30 |
| Active ingredients | 1.10 |
| Preservative | 0.58 |
| Water | ad 100.00 |

Example 45

Decorative lipstick

| | % by wt. |
|---|---|
| PEG-45/dodecyl glycol copolymer | 1.60 |
| Sorbitan isostearate | 2.40 |
| Simethicone | 0.50 |
| Octyldodecanol | 7.00 |
| Polydecene | 4.80 |
| Castor oil | 3.00 |
| *Buxus chinensis* | 1.00 |
| Squalane | 1.00 |
| Macadamia oil | 1.50 |
| *Persea gratissima* | 1.50 |
| Ethylhexyl methoxycinnamate | 2.00 |
| bis-Ethylhexyloxyphenol methoxyphenyltriazine | 0.25 |
| Cetyl palmitate | 1.00 |
| $C_{20-40}$-Alkyl stearate | 8.00 |
| Glycerol | 7.50 |
| Color paste | 11.60 |
| Perfume | 0.30 |
| Active ingredients | 1.10 |
| Preservative | 0.58 |
| Water | ad 100.00 |

Example 46

Concealing stick

| | % by wt. |
|---|---|
| PEG-45/dodecyl glycol copolymer | 1.60 |
| PEG-7 hydrogenated castor oil | 2.40 |
| Simethicone | 0.50 |
| Octyldodecanol | 7.00 |
| Polydecene | 4.80 |
| Castor oil | 3.00 |
| *Buxus chinensis* | 1.00 |
| Squalane | 1.00 |
| Macadamia oil | 1.50 |
| *Persea gratissima* | 1.50 |
| Ethylhexyl methoxycinnamate | 2.00 |
| bis-Ethylhexyloxyphenol methoxyphenyltriazine | 0.25 |
| Cetyl palmitate | 1.00 |
| $C_{20-40}$-Alkyl stearate | 8.00 |
| Glycerol | 7.50 |
| Color paste | 11.60 |
| Perfume | 0.30 |
| Active ingredients | 1.10 |
| Preservative | 0.58 |
| Water | ad 100.00 |

Example 47

Concealing stick stick

| | % by wt. |
|---|---|
| PEG-45/dodecyl glycol copolymer | 1.60 |
| Polyglyceryl-2 dipolyhydroxystearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 48

Kohl pencil

| | % by wt. |
|---|---|
| PEG-45/dodecyl glycol copolymer | 1.60 |
| PEG-40 sorbitan perisostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 49

Kohl pencil

| | % by wt. |
|---|---|
| PEG-45/dodecyl glycol copolymer | 1.60 |
| Glycerol isostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 50

Eyebrow pencil

| | % by wt. |
|---|---|
| PEG-45/dodecyl glycol copolymer | 1.60 |
| Cetyl alcohol | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 51

Eye shadow pencil

| | % by wt. |
|---|---|
| PEG-45/dodecyl glycol copolymer | 1.60 |
| Propylene glycol isostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate, methyl palmitate (9:1) | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 52

Eye shadow pencil

| | % by wt. |
|---|---|
| PEG-45/dodecyl glycol copolymer | 1.60 |
| Isostearyl glycerol ether | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Active ingredients | 1.10 |
| Preservative | 0.58 |
| Water | ad 100.00 |

Example 53

Concealing stick

| | % by wt. |
|---|---|
| PEG-45/dodecyl glycol copolymer | 1.60 |
| Glycerol sorbitan isostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol | 10.00 |
| Color paste | 11.60 |
| Perfume | 0.30 |
| Lipoic acid | 1.00 |
| Preservative | 0.58 |
| Water | ad 100.00 |

Example 54

Concealing stick

| | % by wt. |
|---|---|
| PEG-45/dodecyl glycol copolymer | 1.60 |
| Steareth-2 | 1.60 |

-continued

Concealing stick

| | % by wt. |
|---|---|
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol, chitosan | 10.00 |
| Color paste | 11.60 |
| Perfume | 0.30 |
| Creatine | 1.10 |
| Preservative | 0.58 |
| Water | ad 100.00 |

Example 55

Decorative lipstick

| | % by wt. |
|---|---|
| PEG-45/dodecyl glycol copolymer | 1.60 |
| Propylene glycol isostearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate | 4.50 |
| Glycerol, Fucogel (9:1) | 10.00 |
| Color paste | 11.60 |
| Perfume | 0.30 |
| Coenzyme Q10 (encapsulated in cyclodextrin) | 1.10 |
| Preservative | 0.58 |
| Water | ad 100.00 |

Example 56

Decorative lipstick

| | % by wt. |
|---|---|
| PEG-45/dodecyl glycol copolymer | 1.60 |
| PEG-30 dipolyhydroxystearate | 1.60 |
| Simethicone | 0.50 |
| Octyldodecanol | 7.00 |
| Polydecene | 7.00 |
| Castor oil | 7.00 |
| Butylmethoxydibenzoylmethane | 0.80 |
| 4-Methylbenzylidenecamphor | 1.60 |
| Candelilla cera | 4.50 |
| $C_{20-40}$-Alkyl stearate, cetearyl behenate (9:1) | 4.50 |
| Glycerol, lactic acid (9:1) | 10.00 |
| Color paste | 11.60 |
| Perfume | 0.30 |
| Biotin, coenzyme Q-10 (1:1) | 0.50 |
| Preservative | 0.58 |
| Water | ad 100.00 |

Example 57

Lipcare stick

| | % by wt. |
|---|---|
| PEG-45/dodecyl glycol copolymer | 1.60 |
| Polyglyceryl-3 diisostearate | 1.60 |
| Caprylic/capric triglyceride | 8.60 |
| Octyldodecanol | 8.60 |
| Dicaprylyl ether | 8.60 |
| Castor oil | 5.40 |
| $C_{18-36}$-Acid triglyceride | 15.00 |
| Tocopherol, carnitine (1:1) | 0.20 |
| Glycerol, propylene glycol (9:1) | 10.00 |
| Preservative | 0.58 |
| Water | ad 100.00 |

Example 58

Face care stick with a high water and moisturizer content

| | % by wt. |
|---|---|
| PEG-45/dodecyl glycol copolymer | 1.60 |
| Polyglyceryl-3 diisostearate | 2.40 |
| Octyldodecanol | 9.00 |
| Polydecene | 7.00 |
| *Buxus chinensis* | 1.00 |
| Squalane | 1.00 |
| Ethylhexyl methoxycinnamate | 5.00 |
| bis-Ethylhexyloxyphenol methoxyphenyltriazine | 0.25 |
| $C_{20-40}$-Alkyl stearate | 8.00 |
| Tocopherol acetate | 0.30 |
| PEG-8 beeswax | 1.00 |
| Glycerol, sodium pyrrolidonecarboxylic acid salt (9:1) | 10.00 |
| Perfume | 0.30 |
| Active ingredients | 1.00 |
| Preservative | 0.58 |
| Water | ad 100.00 |

Example 59

Lipcare stick

| | % by wt. |
|---|---|
| PEG-45/dodecyl glycol copolymer | 1.60 |
| Polyglyceryl-3 diisostearate | 2.40 |
| Octyldodecanol | 9.00 |
| Polydecene | 7.00 |
| *Buxus chinensis* | 1.00 |
| Squalane | 1.00 |
| Ethylhexyl methoxycinnamate | 5.00 |
| bis-Ethylhexyloxyphenol methoxyphenyltriazine | 0.25 |
| $C_{20-40}$-Alkyl stearate | 8.00 |
| PEG-8 beeswax | 1.00 |
| Glycerol, hyaluronic acid salt (9:1) | 10.00 |
| Perfume | 0.30 |
| Dioic acid | 0.50 |
| Preservative | 0.58 |
| Water | ad 100.00 |

Example 60

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 11.30 |
| Polydecene | 11.30 |
| Castor oil | 11.30 |
| *Buxus chinensis* | 1.00 |
| Shea butter | 1.00 |
| $C_{20-40}$-Alkyl stearate | 9.00 |
| Glycerol, polyethylene glycol (9:1) | 10.00 |
| Perfume | 0.10 |
| Vitamin C, tocopherol (1:1) | 1.10 |
| Preservative | 0.58 |
| Water | ad 100.00 |

Example 61

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 10.00 |
| Castor oil | 11.30 |
| *Buxus chinensis* | 5.00 |
| Shea butter | 1.00 |
| $C_{20-40}$-Alkyl stearate | 8.00 |
| Glycerol, urea (9:1) | 10.00 |
| Perfume | 0.10 |
| Active ingredients | 1.10 |
| Preservative | 0.58 |
| Water | ad 100.00 |

Example 62

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 5.00 |
| Polydecene | 5.00 |
| Castor oil | 5.00 |
| *Buxus chinensis* | 1.00 |
| *Butyrospermum parkii* | 1.00 |
| *Cera microcristallina* | 2.00 |
| $C_{20-40}$-Alkyl stearate | 6.00 |
| Glycerol, glycine (9:1) | 10.00 |
| Perfume | 0.10 |
| Active ingredients | 1.10 |
| Preservative | 0.58 |
| Water | ad 100.00 |

Example 63

| Lipcare stick | |
|---|---|
| | % by wt. |
| PEG-45/dodecyl glycol copolymer | 1.600 |
| Polyglyceryl-3 diisostearate | 1.60 |
| Octyldodecanol | 5.00 |
| Polydecene | 5.00 |
| Castor oil | 5.00 |
| *Buxus chinensis* | 1.00 |
| *Butyrospermum parkii* | 1.00 |
| Hydrogenated cocoglycerides | 2.00 |
| $C_{20-40}$-Alkyl stearate | 6.00 |
| Glycerol, urea (9:1) | 10.00 |
| Perfume | 0.10 |
| Active ingredients | 1.10 |
| Preservative | 0.58 |
| Water | ad 100.00 |

Example 64

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 5.00 |
| Polydecene | 5.00 |
| Castor oil | 5.00 |
| *Buxus chinensis* | 1.00 |
| *Butyrospermum parkii* | 1.00 |
| Cetyl palmitate | 2.00 |
| $C_{20-40}$-Alkyl stearate | 6.00 |
| Glycerol, NaCl (7:3) | 10.00 |
| Perfume | 0.10 |
| Active ingredients | 1.10 |
| Preservative | 0.58 |
| Water | ad 100.00 |

Example 65

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 5.00 |
| Polydecene | 5.00 |
| Castor oil | 5.00 |
| *Buxus chinensis* | 1.00 |
| *Butyrospermum parkii* | 1.00 |
| Myristyl myristate | 2.00 |
| $C_{20-40}$-Alkyl stearate | 6.00 |
| Glycerol, butylene glycol (9:1) | 10.00 |
| Perfume | 0.10 |
| Active ingredients | 1.10 |
| Preservative | 0.58 |
| Water | ad 100.00 |

Example 66

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 11.45 |
| Hydrogenated polydecene | 11.45 |
| Biosaccharide gum | 5.00 |
| *Buxus chinensis* | 1.00 |
| *Persea Gratissima* | 1.00 |
| Tocopherol acetate | 1.00 |
| Cetyl palmitate | 0.55 |
| $C_{20-40}$-Alkyl stearate | 6.55 |
| Hydrogenated cocoglycerides | 2.20 |
| PVP hexadecene copolymer | 2.00 |
| Squalane | 1.00 |
| Cera alba | 2.20 |
| Panthenol | 0.13 |
| *Butyrospermum parkii* | 1.00 |
| Octocrylene | 3.00 |
| Glycerol, butylene glycol (9:1) | 10.00 |
| Perfume | 0.10 |
| Preservative | 0.58 |
| Water | ad 100.00 |

Example 67

| Lipcare stick | |
|---|---|
| | % by wt. |
| PEG-45/dodecyl glycol copolymer | 1.60 |
| Polyglyceryl-3 diisostearate | 1.60 |
| Octyldodecanol | 11.00 |
| Hydrogenated polydecene | 11.00 |
| Bisaccharide gum | 5.00 |
| *Buxus chinensis* | 1.00 |
| *Persea Gratissima* | 1.00 |
| *Macadamia ternifolia* | 1.00 |
| Tocopherol acetate | 1.00 |
| Cetyl palmitate | 0.50 |
| $C_{20-40}$-Alkyl stearate | 6.00 |
| Hydrogenated cocoglycerides | 2.00 |
| PVP hexadecene copolymer | 2.00 |
| Squalane | 1.00 |
| Cera alba | 2.00 |
| Panthenol | 0.13 |
| *Butyrospermum parkii* | 1.00 |
| Octocrylene | 3.00 |
| Lanolin oil | 2.00 |
| Glycerol | 10.00 |
| Perfume | 0.10 |
| Preservative | 0.58 |
| Water | ad 100.00 |

Example 68

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Cetearyl isononanoate | 5.24 |
| Butylene glycol dicaprylate/dicaprate | 5.24 |
| Ethylhexyl methoxycinnamate | 5.00 |
| bis-Ethylhexyloxyphenol methoxyphenyltriazine | 3.00 |
| Ethylhexyltriazone | 3.00 |
| Titanium dioxide | 4.00 |
| PVP/hexadecene copolymer | 0.50 |
| $C_{20-40}$-Alkyl stearate | 9.00 |
| Glycerol | 10.00 |
| Tocopherol acetate | 1.00 |
| Preservative | 0.58 |
| Water | ad 100.00 |

Example 69

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Cetearyl isononanoate | 5.24 |
| Butylene glycol dicaprylate/dicaprate | 5.24 |
| Ethylhexyl methoxycinnamate | 7.00 |
| bis-Ethylhexyloxyphenol methoxyphenyltriazine | 2.50 |
| Ethylhexyltriazone | 3.00 |
| Titanium dioxide | 2.00 |
| PVP/hexadecene copolymer | 0.50 |
| $C_{20-40}$-Alkyl stearate | 9.00 |
| Glycerol | 10.00 |
| Tocopherol acetate | 1.00 |
| Preservative | 0.58 |
| Water | ad 100.00 |

Example 70

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Cetearyl isononanoate | 5.24 |
| Butylene glycol dicaprylate/dicaprate | 5.24 |
| Ethylhexyl methoxycinnamate | 5.00 |
| bis-Ethylhexyloxyphenol methoxyphenyltriazine | 2.50 |
| Ethylhexyltriazone | 3.00 |
| Titanium dioxide | 4.00 |
| Phenylbenzimidazolesulfonic acid | 2.00 |
| Sodium hydroxide solution | 0.55 |
| PVP/hexadecene copolymer | 0.50 |
| $C_{20-40}$-Alkyl stearate | 9.00 |
| Glycerol | 10.00 |
| Tocopherol acetate | 1.00 |
| Preservative | 0.58 |
| Water | ad 100.00 |

Example 71

Sunscreen stick

| | % by wt. |
|---|---|
| PEG-45/dodecyl glycol copolymer | 1.60 |
| Polyglyceryl-3 diisostearate | 1.60 |
| Caprylic/capric triglyceride | 5.24 |
| Cetearyl isononanoate | 4.10 |
| Butylene glycol dicaprylate/dicaprate | 4.07 |
| Ethylhexyl methoxycinnamate | 5.00 |
| bis-Ethylhexyloxyphenol methoxyphenyltriazine | 2.00 |
| Octocrylene | 5.00 |
| Diethylhexylbutamidotriazone | 2.00 |
| Titanium dioxide | 4.00 |
| PVP/hexadecene copolymer | 0.50 |
| $C_{20-40}$-Alkyl stearate | 9.00 |
| Glycerol | 10.00 |
| Tocopherol acetate | 1.00 |
| Preservative | 0.58 |
| Water | ad 100.00 |

Example 72

Sunscreen stick

| | % by wt. |
|---|---|
| PEG-45/dodecyl glycol copolymer | 1.60 |
| Polyglyceryl-3 diisostearate | 1.60 |
| Cetearyl isononanoate | 15.00 |
| Butylene glycol dicaprylate/dicaprate | 5.00 |
| Ethylhexyl methoxycinnamate | 3.60 |
| Butyl methoxycinnamate | 1.00 |
| Methylbenzylidenecamphor | 3.60 |
| Titanium dioxide | 3.00 |
| $C_{20-40}$-Alkyl stearate | 8.50 |
| Glycerol | 10.00 |
| Preservative | 0.58 |
| Water | ad 100.00 |

Example 73

Sunscreen stick

| | % by wt. |
|---|---|
| PEG-45/dodecyl glycol copolymer | 1.60 |
| Polyglyceryl-3 diisostearate | 1.60 |
| Cetearyl isononanoate | 10.00 |
| Butylene glycol dicaprylate/dicaprate | 5.00 |
| Ethylhexyl methoxycinnamate | 5.00 |
| Ethylhexyltriazone | 3.00 |
| bis-Ethylhexyloxyphenol methoxyphenyltriazine | 2.50 |
| Titanium dioxide | 2.00 |
| $C_{20-40}$-Alkyl stearate | 8.50 |
| Glycerol | 10.00 |
| Preservative | 0.58 |
| Water | ad 100.00 |

Example 74

Sunscreen stick

| | % by wt. |
|---|---|
| PEG-45/dodecyl glycol copolymer | 1.60 |
| Polyglyceryl-3 diisostearate | 1.60 |
| Cetearyl isononanoate | 10.00 |
| Butylene glycol dicaprylate/dicaprate | 5.00 |
| Ethylhexyl methoxycinnamate | 5.00 |
| Ethylhexyltriazone | 3.00 |
| bis-Ethylhexyloxyphenol methoxyphenyltriazine | 2.50 |
| Disodiumphenyldibenzimidazoletetrasulfonate | 0.50 |
| Sodium hydroxide solution | 0.50 |
| Titanium dioxide | 2.00 |
| $C_{20-40}$-Alkyl stearate | 8.50 |
| Glycerol | 10.00 |
| Preservative | 0.50 |
| Water | ad 100.00 |

Example 75

Sunscreen stick

| | % by wt. |
|---|---|
| PEG-45/dodecyl glycol copolymer | 1.60 |
| Polyglyceryl-3 diisostearate | 1.60 |
| Cetearyl isononanoate | 5.00 |
| Caprylic/capric triglyceride | 5.00 |
| Butylene glycol dicaprylate/dicaprate | 5.00 |
| Ethylhexyl methoxycinnamate | 5.00 |
| Ethylhexyltriazone | 3.00 |
| bis-Ethylhexyloxyphenol methoxyphenyltriazine | 2.50 |
| Titanium dioxide | 2.00 |
| $C_{20-40}$-Alkyl stearate | 8.50 |
| Glycerol, sodium pyrrolidonecarboxylic acid salt (9:1) | 10.00 |
| Preservative | 0.58 |
| Water | ad 100.00 |

Example 76

Sunscreen stick

| | % by wt. |
|---|---|
| PEG-45/dodecyl glycol copolymer | 1.60 |
| Polyglyceryl-3 diisostearate | 1.60 |
| Cetearyl isononanoate | 10.00 |
| Butylene glycol dicaprylate/dicaprate | 5.00 |
| Ethylhexyl methoxycinnamate | 5.00 |
| Ethylhexyltriazone | 3.00 |
| bis-Ethylhexyloxyphenol methoxyphenyltriazine | 2.50 |
| Titanium dioxide | 2.00 |
| $C_{20-40}$-Alkyl stearate | 6.00 |
| $C_{18-36}$-Acid triglyceride | 4.00 |
| Glycerol, hyaluronic acid salt (9:1) | 10.00 |
| Active ingredients (glyosylrutin) | 0.50 |
| Preservative | 0.58 |
| Water | ad 100.00 |

Example 77

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Simethicone | 0.50 |
| Glycerol, glycine (9:1) | 10.00 |
| Cetearyl isononanoate | 5.24 |
| PVP/hexadecene copolymer | 0.50 |
| PEG-8 beeswax | 0.50 |
| $C_{20-40}$-Alkyl stearate | 8.50 |
| Butylene glycol dicaprylate/dicaprate | 5.24 |
| Active ingredient (Q-10) | 0.50 |
| Preservative | 0.58 |
| Ethylhexyl methoxycinnamate | 5.00 |
| Ethylhexyltriazone | 3.00 |
| Titanium dioxide + trimethoxycaprylylsilane | 4.00 |
| bis-Ethylhexylphenol methoxyphenyltriazine | 2.50 |
| Water | ad 100.00 |

Example 78

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Simethicone | 0.50 |
| Glycerol, urea (9:1) | 10.00 |
| Cetearyl isononanoate | 5.24 |
| PVP/hexadecene copolymer | 0.50 |
| $C_{20-40}$-Alkyl stearate | 8.50 |
| Carnauba wax | 0.50 |
| Butylene glycol dicaprylate/dicaprate | 5.24 |
| Active ingredient (lipoic acid, carnithine 1:1) | 1.00 |
| Preservative | 0.58 |
| Ethylhexyl methoxycinnamate | 7.00 |
| Ethylhexyltriazone | 3.00 |
| Titanium dioxide | 2.00 |
| bis-Ethylhexylphenol methoxyphenyltriazine | 2.50 |
| Water | ad 100.00 |

Example 79

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 5.24 |
| Simethicone | 0.50 |
| Glycerol, polyethylene glycol (9:1) | 10.00 |
| Cetearyl isononanoate | 5.24 |
| PVP/hexadecene copolymer | 0.50 |
| $C_{20-40}$-Alkyl stearate | 9.00 |
| Methyl palmitate | 1.00 |
| Butylene glycol dicaprylate/dicaprate | 5.24 |
| Active ingredient (creatine) | 1.00 |

-continued

| Sunscreen stick | |
|---|---|
| | % by wt. |
| Preservative | 0.58 |
| Ethylhexyl methoxycinnamate | 5.00 |
| Phenylbenzimidazolesulfonic acid | 2.00 |
| Sodium hydroxide solution (105) | 0.55 |
| Ethylhexyltriazone | 3.00 |
| Titanium dioxide | 2.00 |
| bis-Ethylhexylphenol methoxyphenyltriazine | 2.50 |
| Water | ad 100.00 |

Example 80

| Sunscreen stick | |
|---|---|
| | % by wt. |
| PEG-45/dodecyl glycol copolymer | 1.60 |
| Polyglyceryl-3 diisostearate | 1.60 |
| Caprylic/capric triglyceride | 4.41 |
| Simethicone | 0.50 |
| Glycerol, Fucogel | 10.00 |
| Cetearyl isononanoate | 4.41 |
| PVP/hexadecene copolymer | 0.50 |
| $C_{20-40}$-Alkyl stearate | 9.00 |
| Butylene glycol dicaprylate/dicaprate | 4.41 |
| Active ingredient (adenosine) | 1.00 |
| Preservative | 0.58 |
| Ethylhexyl methoxycinnamate | 5.00 |
| Titanium dioxide | 2.00 |
| Octocrylene | 5.00 |
| bis-Ethylhexylphenol methoxyphenyltriazine | 2.00 |
| Diethylhexylbutamidotriazone | 3.00 |
| Water | ad 100.00 |

Example 81

| Sunscreen stick or aftersun stick | |
|---|---|
| | % by wt. |
| PEG-45/dodecyl glycol copolymer | 1.60 |
| Polyglyceryl-3 diisostearate | 1.60 |
| Caprylic/capric triglyceride | 4.07 |
| Simethicone | 0.50 |
| Glycerol, sodium chloride (5:5) | 10.00 |
| Cetearyl isononanoate | 4.07 |
| PVP/hexadecene copolymer | 0.50 |
| $C_{20-40}$-Alkyl stearate | 9.00 |
| Butylene glycol dicaprylate/dicaprate | 4.07 |
| Active ingredient (tocopherol, vitamin C 1:3) | 4.00 |
| Preservative | 0.58 |
| Ethylhexyl methoxycinnamate | 5.00 |
| Octocrylene | 5.00 |
| Titanium dioxide | 4.00 |
| bis-Ethylhexylphenol methoxyphenyltriazine | 2.00 |
| Diethylhexylbutamidotriazone | 2.00 |
| Water | ad 100.00 |

Example 82

Sunscreen stick or aftersun stick

| | % by wt. |
|---|---|
| PEG-45/dodecyl glycol copolymer | 1.60 |
| Sorbitan isostearate | 1.60 |
| Caprylic/capric triglyceride | 4.40 |
| Simethicone | 0.50 |
| Glycerol | 10.00 |
| Cetearyl isononanoate | 4.40 |
| PVP/hexadecene copolymer | 0.50 |
| $C_{20-40}$-Alkyl stearate | 9.00 |
| Butylene glycol dicaprylate/dicaprate | 4.40 |
| Active ingredient (biotin, tocopherol, 1:1) | 1.00 |
| Preservative | 0.58 |
| Ethylhexyl methoxycinnamate | 7.00 |
| Ethylhexyltriazone | 3.00 |
| Titanium dioxide | 4.00 |
| bis-Ethylhexylphenol methoxyphenyltriazine | 2.50 |
| Perfume | 0.50 |
| Water | ad 100.00 |

Example 83

Sunscreen stick or aftersun stick

| | % by wt. |
|---|---|
| PEG-45/dodecyl glycol copolymer | 1.60 |
| PEG-30 dipolyhydroxystearate | 1.60 |
| Caprylic/capric triglyceride | 4.57 |
| Simethicone | 0.50 |
| Glycerol | 10.00 |
| Dicaprylyl carbonate | 4.57 |
| PVP/hexadecene copolymer | 0.50 |
| $C_{20-40}$-Alkyl stearate | 9.00 |
| Butylene glycol dicaprylate/dicaprate | 4.57 |
| Active ingredient (panthenol, tocopherol 1:1) | 1.00 |
| Preservative | 0.58 |
| Ethylhexyl methoxycinnamate + BHT | 5.00 |
| Phenylbenzimidazolesulfonic acid | 2.00 |
| Sodium hydroxide solution (10%) | 0.55 |
| Ethylhexyltriazone | 3.00 |
| bis-Ethylhexylphenol methoxyphenyltriazine | 2.00 |
| Titanium dioxide + alumina + simethicone + aqua | 4.00 |
| Perfume | 0.50 |
| Water | ad 100.00 |

Example 84

Sunscreen stick

| | % by wt. |
|---|---|
| PEG-45/dodecyl glycol copolymer | 1.60 |
| Polyglyceryl-3 diisostearate | 1.60 |
| Caprylic/capric triglyceride | 4.40 |
| Simethicone | 0.50 |
| Glycerol | 10.00 |
| Cetearyl isononanoate, $C_{12-15}$-alkylbenzoate (1.1) | 4.40 |
| PVP/hexadecene copolymer | 0.50 |
| $C_{20-40}$-Alkyl stearate | 9.00 |
| Butylene glycol dicaprylate/dicaprate | 4.40 |
| Active ingredient (zinc salt, bisabolol 1:1) | 1.00 |
| Preservative | 0.58 |
| Ethylhexyl methoxycinnamate | 7.00 |
| Ethylhexyltriazone | 3.000 |
| bis-Ethylhexylphenol methoxyphenyltriazine | 2.50 |
| Titanium dioxide + alumina + simethicone + aqua | 4.00 |
| Perfume | 0.50 |
| Water | ad 100.00 |

Example 85

Sunscreen stick

| | % by wt. |
|---|---|
| PEG-45/dodecyl glycol copolymer | 1.60 |
| Polyglyceryl-3 methylglucose distearate | 1.60 |
| Caprylic/capric triglyceride | 5.07 |
| Simethicone | 0.50 |
| Glycerol | 10.00 |
| Cetearyl isononanoate, lanolin oil | 5.07 |
| PVP/hexadecene copolymer | 0.50 |
| $C_{20-40}$-Alkyl stearate | 9.00 |
| Butylene glycol dicaprylate/dicaprate | 5.07 |
| Active ingredient | 1.00 |
| Preservative | 0.58 |
| Ethylhexyl methoxycinnamate | 5.00 |
| Ethylhexyltriazone | 3.00 |
| bis-Ethylhexylphenol methoxyphenyltriazine | 2.50 |
| Titanium dioxide + alumina + simethicone + aqua | 4.00 |
| Perfume | 0.50 |
| Water | ad 100.00 |

Example 86

Sunscreen stick

| | % by wt. |
|---|---|
| PEG-45/dodecyl glycol copolymer | 1.60 |
| Polyglyceryl-3 diisostearate | 1.60 |
| Caprylic/capric triglyceride, cocoglyceride | 4.74 |
| Simethicone | 0.50 |
| Glycerol | 10.00 |
| Cetearyl isononanoate | 4.74 |
| PVP/hexadecene copolymer | 0.50 |
| $C_{20-40}$-Alkyl stearate | 9.00 |
| Butylene glycol dicaprylate/dicaprate | 4.74 |
| Active ingredient (tocopherol acetate) | 1.00 |
| Preservative | 0.58 |
| Ethylhexyl methoxycinnamate | 5.00 |
| Ethylhexyltriazone | 3.00 |
| bis-Ethylhexylphenol methoxyphenyltriazine | 2.50 |
| Silica dimethyl silylate | 1.00 |
| Titanium dioxide + alumina + simethicone + aqua | 4.00 |
| Perfume | 0.50 |
| Water | ad 100.00 |

Example 87

Sunscreen stick

| | % by wt. |
|---|---|
| PEG-45/dodecyl glycol copolymer | 1.60 |
| Polyglyceryl-3 diisostearate | 1.60 |
| Caprylic/capric triglyceride | 5.24 |
| Cetearyl isononanoate | 5.24 |
| Butylene glycol dicaprylate/dicaprate | 5.24 |
| Ethylhexyl methoxycinnamate | 5.00 |
| bis-Ethylhexyloxyphenol methoxyphenyltriazine | 3.00 |
| Ethylhexyltriazone | 3.00 |
| Titanium dioxide* and propylene glycol | 2.00 |
| PVP/hexadecene copolymer | 0.50 |
| $C_{20-40}$-Alkyl stearate | 9.00 |
| Glycerol | 10.00 |
| Tocopherol acetate | 1.00 |
| Preservative | 0.58 |
| Water | ad 100.00 |

Water-dispersible titanium dioxide: Tioveil AQ+10% propylene glycol from Tioxid Specalities

Example 88

Skin-lightening stick

| | % by wt. |
|---|---|
| Caprylic/capric triglyceride | 14.6666 |
| Aqua | 61.5534 |
| Glycerol | 10 |
| Phenoxyethanol | 0.5 |
| PEG-45/dodecyl glycol copolymer | 1.6 |
| Polyglyceryl-3 diisostearate | 1.6 |
| $C_{20-40}$-Alkyl stearate | 9 |
| Hexamidine diisethionate | 0.08 |
| 8-Hexadecene-1,16-dicarboxylic acid | 1 |

Examples 89-91

Silk Shimmer Sticks

Example 92

Care Stick

| | 89% by wt. | 90% by wt. | 91% by wt. | 92% by wt. |
|---|---|---|---|---|
| Butylene glycol dicaprylate/dicaprate | 8.1120 | 4.7735 | 4.7735 | 4.7735 |
| $C_{18-36}$ Fatty acid triglycerides | 0.6000 | 1.1000 | 1.1000 | 1.1000 |
| $C_{20-40}$ Alkyl stearate | 11.4000 | 20.9000 | | |
| Caprylic/capric triglyceride | 8.3110 | 4.7730 | 4.7730 | 4.7730 |
| Cetearyl isononanoate | 8.1120 | 4.7735 | 4.7735 | 4.7735 |
| Perfume | 0.4000 | 0.4000 | 0.4000 | 0.4000 |
| Glycerol | 10.0000 | 10.0000 | 10.0000 | 10.0000 |
| Hexamidine diisethionate | 0.0800 | 0.0800 | 0.0800 | 0.0800 |
| PEG-45/dodecyl glycol copolymer | 1.6000 | 1.6000 | 1.6000 | 1.6000 |
| Phenoxyethanol | 0.5000 | 0.5000 | 0.5000 | 0.5000 |
| Polyethylene (Performalene 400) | | | 20.9000 | 20.9000 |
| Polyglyceryl-3 diisostearate | 1.6000 | 1.6000 | 1.6000 | 1.6000 |
| Simethicone | 0.5000 | 0.5000 | 0.5000 | 0.5000 |
| Titanium dioxide + iron oxide + mica | 0.5000 | 0.5000 | 0.5000 | |
| Titanium dioxide + mica + tin oxide | 3.0000 | 3.0000 | 3 | |
| Water | ad 100 | ad 100 | ad 100 | ad 100 |

Examples 93-97

| | 93 Care stick | 94 Concealing stick | 95 Foundation stick | 96 Sunscreen stick | 97 Blusher stick |
|---|---|---|---|---|---|
| Caprylic/capric triglyceride | 8 | 5 | 5 | 8 | 3 |
| Octyldodecanol | 7 | 5 | 5 | 8 | 6 |
| Caprylyl carbonate | | | 3 | | |
| Dicaprylyl ether | | | 2 | | |
| Paraffin oil | 2 | | | | 1 |
| Pentaerythrityl tetraisostearate | 2 | 4 | | 8 | |
| $C_{12-15}$ Alkyl benzoate | 2 | | | | |
| Isopropyl palmitate | | | | | 2 |
| Jojoba oil | 2 | | | 1 | 1 |
| Lanolin oil | | | | | 1 |
| Simethicone | | 0.5 | 0.5 | | 0.5 |
| PEG-45/dodecyl glycol copolymer | 3 | 3.5 | 2 | 2 | 2 |
| Polyglyceryl-3 diisostearate | 2.5 | | 1.5 | 2 | 2.4 |
| PEG-30 dipolyhydroxy-stearate | | | | 2.5 | |
| Sucrose distearate | 0.5 | | | | |
| bis-Diglyceryl polyacyladipate-2 | 9 | 2 | | | |
| Cetyl palmitate | 2.5 | | | | 1 |
| $C_{16-36}$ Alkyl stearate | 14 | 1 | 2 | 1 | |
| $C_{20-40}$ Alkyl stearate | | 8 | 8 | 9 | 8 |
| Carnauba wax | 1.5 | 1.5 | | | 2 |
| Beeswax | 0.5 | | | | |
| Candelilla wax | | | | | 1 |
| PVP/eicosene copolymer | | 1 | | 1 | 0.2 |

-continued

| | 93 Care stick | 94 Concealing stick | 95 Foundation stick | 96 Sunscreen stick | 97 Blusher stick |
|---|---|---|---|---|---|
| Butylmethoxydibenzoyl-methane | | | | 1 | |
| Micronized titanium dioxide | | 2 | | 4 | |
| 4-Methylbenzylidenecamphor | | | | 3.6 | 5 |
| Octyl methoxycinnamate | | 2 | | 3.6 | 2.5 |
| Nylon-12 | | 3 | | | |
| Bismuth oxychloride (BiOCl) | 2 | | 3 | | 2 |
| Boron nitride | | | | 3 | 1 |
| Lauroyl lysine | | 0.5 | | | |
| Polymethylsilsesquioxane (Tospearl) | | | 0.5 | 1 | |
| Silica LDP | | | | 1 | |
| PTFE | 2.5 | | | | |
| PMMA | | 6 | 3 | | |
| Titanium dioxide Al$_2$O$_3$ coated | | 7 | 6 | | 2 |
| Iron oxide | | 4 | 4 | | 6 |
| Ultramarine | | 0.5 | 0.6 | | |
| Pearlescent pigments | 3 | | | | 2 |
| Rokonsal S1 | 0.4 | | | | |
| Germall II | | 0.25 | | | 0.25 |
| Glydant Plus | | | | 0.3 | |
| JM Acti Care | | | 0.05 | | |
| Glycerol | 5 | 2 | 10 | 5 | 10 |
| Perfume, BHT, neutralizing agent, sequestrant | q.s | q.s | q.s | q.s | q.s |
| Water | ad 100 | ad 100 | ad 100 | ad 100 | ad 100 |

What is claimed is:

1. A water-in-oil emulsion, wherein the emulsion is solid at room temperature and comprises:
   (a) a fatty phase which comprises
      (a1) at least one oil component, and
      (a2) at least one wax component;
   (b) a water phase which comprises
      (b1) from 30% to 85% by weight of water, based on the total weight of the emulsion, and
      (b2) from 5% to 50% by weight, based on the total weight of the emulsion, of at least one skin-moisturizing agent selected from glycerol, chitosan, Fucogel, propylene glycol, polyethylene glycol, dipropylene glycol, butylene glycol, mannitol, lactic acid, glycine, sodium pyrrolidonecarboxylic acid, hyaluronic acid, urea, and salts thereof; and
   (c) at least one water-in-oil emulsifier selected from surface-active substances of the formula A-B-A', where A and A' are identical or different hydrophobic organic radicals, and B is a hydrophilic group.

2. The emulsion of claim 1, wherein (b2) comprises at least 5% by weight of glycerol.

3. The emulsion of claim 2, wherein (b2) further comprises at least one skin-moisturizing agent selected from chitosan, Fucogel, propylene glycol, polyethylene glycol, dipropylene glycol, butylene glycol, mannitol, lactic acid, glycine, sodium pyrrolidonecarboxylic acid, hyaluronic acid, urea, and salts thereof.

4. The emulsion of claim 1, wherein (b2) comprises at least one of chitosan, Fucogel, polyethylene glycol, dipropylene glycol, butylene glycol, mannitol, sodium pyrrolidonecarboxylic acid, urea, and salts thereof.

5. The emulsion of claim 2, wherein (b2) comprises a total of at least 7.5% by weight of glycerol and an agent selected from chitosan, Fucogel, propylene glycol, polyethylene glycol, butylene glycol, sodium pyrrolidonecarboxylic acid, hyaluronic acid, urea, and salts thereof.

6. The emulsion of claim 2, wherein the emulsion comprises at least 35% by weight of water.

7. The emulsion of claim 1, wherein the emulsion comprises at least 45% by weight of water.

8. The emulsion of claim 1, wherein in the at least one water-in-oil emulsifier (c) A and A' are selected from (i) branched and unbranched, saturated and unsaturated alkyl and acyl groups and hydroxyacyl groups having 10-30 carbon atoms, and (ii) hydroxyacyl groups joined together via ester functions, according to the formula

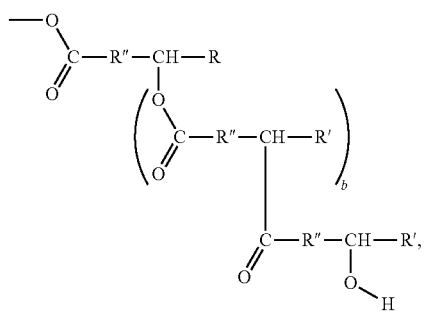

where R' is selected from branched and unbranched alkyl groups having from 1 to 20 carbon atoms, R" is selected from branched and unbranched alkylene groups having from 1 to 20 carbon atoms, and b has a value of from 0 to 200.

9. The emulsion of claim 1, wherein the at least one water-in-oil emulsifier (c) comprises at least one of PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methylglucose distearate and steareth-2.

10. The emulsion of claim 1, wherein the emulsion further comprises a stabilizer selected from substances of formula

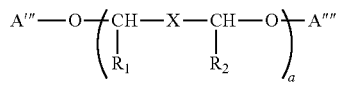

wherein
A''' and A'''' are identical or different hydrophobic organic radicals selected from alkyl radicals, acyl radicals and radicals of formula:

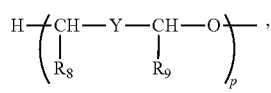

wherein
$R_8$ and $R_9$ may be identical or different and are selected from saturated and unsaturated alkyl and acyl radicals having 1-30 carbon atoms, p is a number of from 1-20, and Y represents a single bond or the group

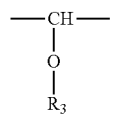

a is a number of from 1 to 100,
X is a single bond or the group

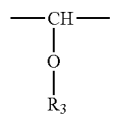

$R_1$ and $R_2$, independently of one another, are H or methyl, with the proviso that $R_1$ and $R_2$ are not both methyl at the same time,
$R_3$ is selected from H and branched and unbranched, saturated and unsaturated alkyl and acyl radicals having 1-30 carbon atoms.

11. The emulsion of claim 10, wherein the stabilizer comprises one or more of a PEG-45/dodecyl glycol copolymer, a PEG-22/dodecyl glycol copolymer, and a methoxy PEG-22/dodecyl glycol copolymer.

12. The emulsion of claim 1, wherein the emulsion further comprises at least one anti-wrinkle substance.

13. A cosmetic or dermatological stick, wherein the stick comprises the water-in-oil emulsion of claim 1.

14. The stick of claim 13, wherein the stick is spreadable and storage-stable in a temperature range of from −10° C. to 50° C.

15. The stick of claim 13, wherein the stick is present in a sleeve-like packaging.

16. The stick of claim 15, wherein the sleeve-like packaging can be filled on both sides from top and bottom.

17. A cosmetic or dermatological stick, wherein the stick comprises a water-in-oil emulsion which is solid at room temperature and comprises:
(a) a fatty phase which comprises
  (a1) at least one oil component, and
  (a2) at least one wax component;
(b) a water phase which comprises
  (b1) from 35% to 85% by weight of water, based on the total weight of the emulsion, and
  (b2) from 5% to 50% by weight, based on the total weight of the emulsion, of at least one skin-moisturizing agent selected from glycerol, chitosan, Fucogel, propylene glycol, polyethylene glycol, butylene glycol, sodium pyrrolidonecarboxylic acid, urea, and salts thereof, provided that at least 5% by weight of glycerol are present, and
(c) at least one water-in-oil emulsifier selected from surface-active substances of the formula A-B-A', where A and A' are identical or different hydrophobic organic radicals, and B is a hydrophilic group;
and wherein the emulsion is capable of being filled into a sleeve-like packaging at a temperature of 90° C.

18. The emulsion of claim 17, wherein (b2) comprises a total of at least 7.5% by weight of glycerol and an agent selected from chitosan, Fucogel, propylene glycol, polyethylene glycol, butylene glycol, sodium pyrrolidonecarboxylic acid, urea, and salts thereof.

19. The emulsion of claim 18, wherein the emulsion comprises at least 45% by weight of water.

20. The emulsion of claim 19, wherein (b2) comprises one of chitosan, Fucogel, sodium pyrrolidonecarboxylic acid, and salts thereof.

* * * * *